US012288332B2

(12) United States Patent
Horiuchi et al.

(10) Patent No.: US 12,288,332 B2
(45) Date of Patent: Apr. 29, 2025

(54) IMAGING SUPPORT APPARATUS, OPERATION METHOD OF IMAGING SUPPORT APPARATUS, AND OPERATION PROGRAM OF IMAGING SUPPORT APPARATUS

(71) Applicant: FUJIFILM CORPORATION, Tokyo (JP)

(72) Inventors: Hisatsugu Horiuchi, Tokyo (JP); Koji Taninai, Tokyo (JP); Masataka Sugahara, Tokyo (JP); Yuji Kai, Tokyo (JP); Yuji Jibiki, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 266 days.

(21) Appl. No.: 18/170,528

(22) Filed: Feb. 17, 2023

(65) Prior Publication Data
US 2023/0274425 A1    Aug. 31, 2023

(30) Foreign Application Priority Data
Feb. 28, 2022    (JP) .................................. 2022-030381

(51) Int. Cl.
*G06T 7/168* (2017.01)
*A61B 6/00* (2006.01)
(Continued)

(52) U.S. Cl.
CPC .............. *G06T 7/0012* (2013.01); *A61B 6/40* (2013.01); *A61B 6/4283* (2013.01); *A61B 6/488* (2013.01);
(Continued)

(58) Field of Classification Search
CPC .. G01N 5/1429; G01N 5/1433; G01N 5/1431; G01N 2015/144; G01N 2015/1445; A61B 6/00; A61B 6/04; A61B 6/12; A61B 6/40; A61B 6/4007; A61B 6/4014; A61B 6/42; A61B 6/4208; A61B 6/4283; A61B 6/54; A61B 6/547; A61B 6/506; A61B 6/0492; A61B 6/0407; G06T 1/0007; G06T 1/0014; G06T 3/14; G06T 7/30;
(Continued)

(56) References Cited

FOREIGN PATENT DOCUMENTS

JP         2020-192440 A    12/2020
WO    WO-2020025110 A1 *    2/2020    ............... A61B 6/04

* cited by examiner

*Primary Examiner* — Don K Wong
(74) *Attorney, Agent, or Firm* — SOLARIS Intellectual Property Group, PLLC

(57) ABSTRACT

A first acquisition unit acquires an optical image in which both an electronic cassette in which a detection panel for detecting radiation is built in a portable housing and a subject facing radiography using the electronic cassette are shown, from a camera. A first demarcation unit demarcates a detection region of the radiation by the detection panel, the detection region being determined in accordance with a position of the electronic cassette, in the optical image. A second demarcation unit demarcates an imaging region which is a region to be imaged in the radiography, the imaging region being determined in accordance with a position of the subject, in the optical image. A display controller performs control of displaying a frame indicating the detection region and a frame indicating the imaging region on a touch panel display in a manner of being superimposed on the optical image.

6 Claims, 18 Drawing Sheets

(51) Int. Cl.
*A61B 6/40* (2024.01)
*A61B 6/42* (2024.01)
*G03B 17/26* (2021.01)
*G06T 1/20* (2006.01)
*G06T 7/00* (2017.01)
*H04N 23/51* (2023.01)
*H04N 23/611* (2023.01)
*A61B 6/46* (2024.01)

(52) U.S. Cl.
CPC .............. *G03B 17/265* (2013.01); *G06T 1/20* (2013.01); *H04N 23/51* (2023.01); *H04N 23/611* (2023.01); *A61B 6/461* (2013.01)

(58) Field of Classification Search
CPC .... G06T 7/32; G06T 7/38; G06T 7/70; G06T 7/80; G06T 7/97
See application file for complete search history.

IMAGING SUPPORT APPARATUS, OPERATION METHOD OF IMAGING SUPPORT APPARATUS, AND OPERATION PROGRAM OF IMAGING SUPPORT APPARATUS

CROSS-REFERENCE TO RELATED APPLICATIONS

The present application claims priority under 35 U.S.C. § 119 to Japanese Patent Application No. 2022-030381, filed on Feb. 28, 2022. The above application is hereby expressly incorporated by reference, in its entirety, into the present application.

BACKGROUND

1. Technical Field

The technology of the present disclosure relates to an imaging support apparatus, an operation method of an imaging support apparatus, and an operation program of an imaging support apparatus.

2. Description of the Related Art

There is known an electronic cassette in which a detection panel for detecting radiation is built in a portable housing. The electronic cassette is used in a state of being accommodated in a holder of an imaging table installed in a radiography room, and is mainly used as a single unit in a state of being removed from the holder by taking advantage of its mobility. For example, the electronic cassette is used in a case of round-visit imaging in which the radiography is performed by traveling around a hospital room in which there is a patient who cannot go to the radiography room. In addition, the electronic cassette may be taken out of a medical facility for the radiography of an elderly person undergoing medical treatment at home or a suddenly ill person due to an accident, disaster, or the like.

JP2020-192440A discloses the technology in which an optical image in which both an electronic cassette and a subject facing radiography using the electronic cassette are shown is acquired from a camera, a position of the electronic cassette in the optical image is detected, and a frame indicating the electronic cassette based on the detected position is displayed on a display in a manner of being superimposed on the optical image. In a tenth embodiment, an aspect is described in which, in a case in which the subject lies down on a bed is subjected to the radiography, a frame indicating a recommended installation position (referred to as a recommended position in JP2020-192440A) of the electronic cassette on the bed is displayed on the display in a manner of being superimposed on the optical image together with the frame indicating the electronic cassette.

SUMMARY

In the radiography using the electronic cassette, the installation position of the electronic cassette can be freely set. Therefore, there is a concern that a situation occurs in which an error is made in the installation position of the electronic cassette with respect to the subject and the imaging is performed in a state in which the electronic cassette does not cover an imaging region to be imaged in the radiography.

In JP2020-192440A, in order to avoid a situation in which the imaging is performed in a state in which the imaging region is not covered by the electronic cassette, the frame indicating the recommended position is displayed in a manner of being superimposed on the optical image. However, JP2020-192440A does not discloses how the recommended position is set, and also how the recommended position is related to the imaging region. Therefore, there is insufficient solution as a solution for avoiding the situation in which the imaging is performed in a state in which the imaging region is not covered by the electronic cassette.

One embodiment according to the technology of the present disclosure provides an imaging support apparatus, an operation method of an imaging support apparatus, and an operation program of an imaging support apparatus capable of contributing to more accurate positioning of the electronic cassette with respect to the subject.

The present disclosure relates to an imaging support apparatus comprising a processor, in which the processor acquires an optical image in which both an electronic cassette in which a detection panel for detecting radiation is built in a portable housing and a subject facing radiography using the electronic cassette are shown, from a camera, demarcates a detection region of the radiation by the detection panel, the detection region being determined in accordance with a position of the electronic cassette, in the optical image, demarcates an imaging region which is a region to be imaged in the radiography, the imaging region being determined in accordance with a position of the subject, in the optical image, and performs control of displaying an indicator indicating the detection region and an indicator indicating the imaging region on a display in a manner of being superimposed on the optical image.

It is preferable that the processor demarcate the detection region based on a detection result of a position detection sensor that detects the position of the electronic cassette.

It is preferable that the processor extract a portion of interest of the subject included in the optical image, and demarcate the imaging region based on the portion of interest.

It is preferable that, in a state in which the subject lies down on a bed, in a case in which the electronic cassette is inserted between the subject and the bed and the radiography is performed, the processor operate an optical display that displays light for position adjustment of the electronic cassette on a side portion along a long side direction of the bed to display an insertion position of the electronic cassette corresponding to the imaging region.

The present disclosure relates to an operation method of an imaging support apparatus, the method comprising acquiring an optical image in which both an electronic cassette in which a detection panel for detecting radiation is built in a portable housing and a subject facing radiography using the electronic cassette are shown, from a camera, demarcating a detection region of the radiation by the detection panel, the detection region being determined in accordance with a position of the electronic cassette, in the optical image, demarcating an imaging region which is a region to be imaged in the radiography, the imaging region being determined in accordance with a position of the subject, in the optical image, and performing control of displaying an indicator indicating the detection region and an indicator indicating the imaging region on a display in a manner of being superimposed on the optical image.

The present disclosure relates to an operation program of an imaging support apparatus, the program causing a computer to execute a process comprising acquiring an optical image in which both an electronic cassette in which a detection panel for detecting radiation is built in a portable housing and a subject facing radiography using the electronic cassette are shown, from a camera, demarcating a detection region of the radiation by the detection panel, the detection region being determined in accordance with a position of the electronic cassette, in the optical image, demarcating an imaging region which is a region to be imaged in the radiography, the imaging region being determined in accordance with a position of the subject, in the optical image, and performing control of displaying an indicator indicating the detection region and an indicator indicating the imaging region on a display in a manner of being superimposed on the optical image.

According to the technology of the present disclosure, it is possible to provide the imaging support apparatus, the operation method of the imaging support apparatus, and the operation program of the imaging support apparatus capable of contributing to more accurate positioning of the electronic cassette with respect to the subject.

BRIEF DESCRIPTION OF THE DRAWINGS

Exemplary embodiments according to the technique of the present disclosure will be described in detail based on the following figures, wherein.

DETAILED DESCRIPTION

First Embodiment

Figure 1:
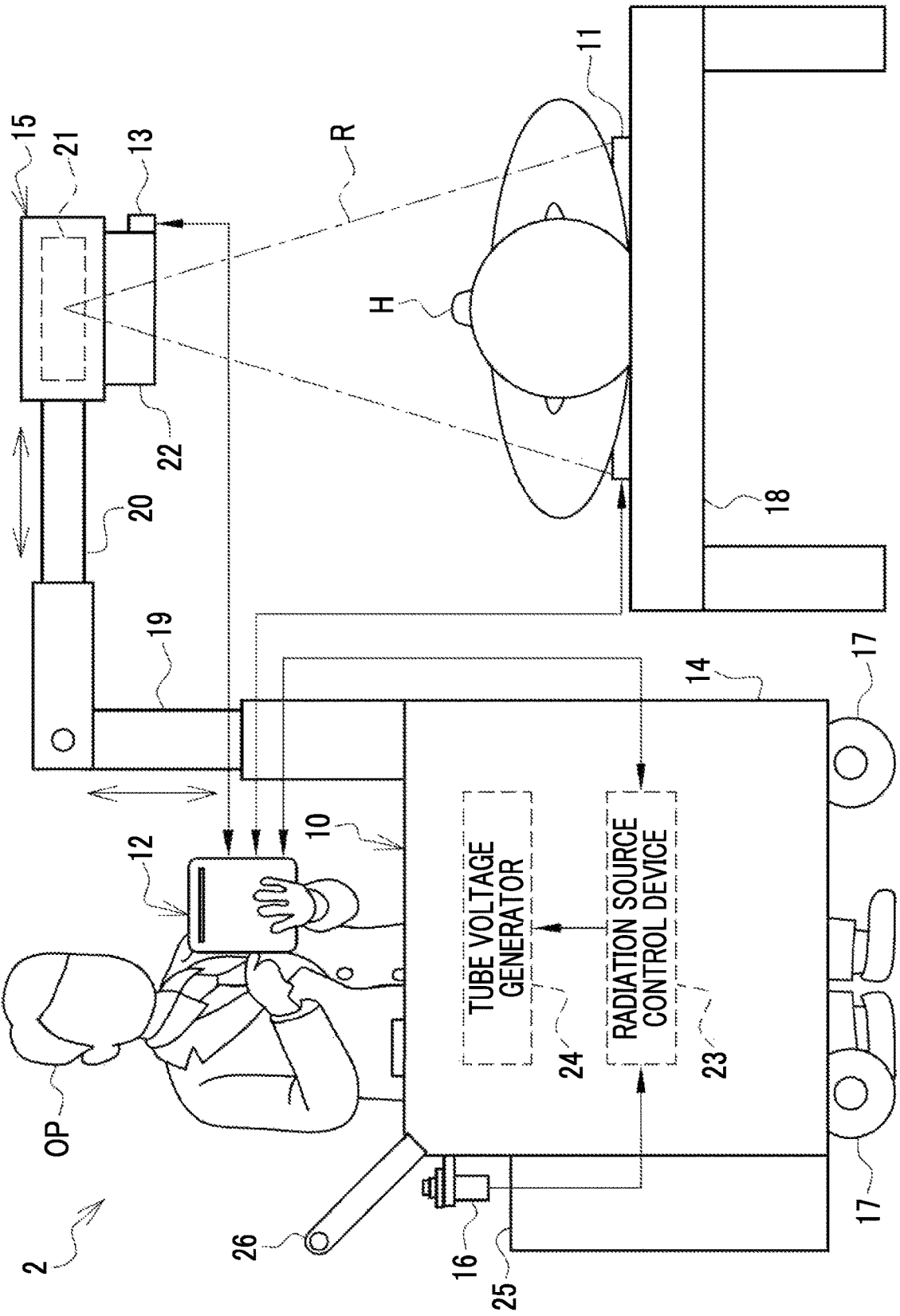
FIG. 1 is a diagram showing a radiography system.

As shown in FIG. 1 as an example, a radiography system 2 is a system that performs radiography of a subject H by using radiation R, such as X-rays and γ-rays, and includes a mobile radiation generation device 10, an electronic cassette 11, a console 12, and a camera 13. The mobile radiation generation device 10 includes a carriage unit 14, a radiation source 15, and an irradiation switch 16. The carriage unit 14 is a rectangular parallelepiped block, and four wheels 17 are attached to the front, rear, left, and right sides below the block. With the wheels 17, the mobile radiation generation device 10 can be used for round-visit imaging in which the radiography of the subject H is performed while traveling around a hospital room in a medical facility. Therefore, the mobile radiation generation device 10 is also referred to as a round-visit vehicle.

FIG. 1 shows a state in which chest portion front surface imaging of the subject H lying down on a bed 18 in the hospital room is performed. In this case, the electronic cassette 11 is inserted between the subject H and the bed 18 by an operator OP, such as a medical radiologist. That is, in the present example, the electronic cassette 11 is not used in a state of being accommodated in a holder of an imaging table installed in a radiography room, and is removed from the holder and used as a single unit. The radiography performed by using the electronic cassette 11 as a single unit in this way is called free imaging. It should be noted that the mobile radiation generation device 10 can also be brought into a surgery room and used during the surgery. In addition, the mobile radiation generation device 10 can also be brought to an outdoor disaster site or the like and used for emergency use.

The radiation source 15 is attached to the carriage unit 14 via a first arm 19 and a second arm 20. The first arm 19 extends in a vertical direction from the center of a front portion of an upper surface of the carriage unit 14. The first arm 19 can be expanded and contracted in the vertical direction. Along with the expansion and contraction of the first arm 19, a height position of the radiation source 15 is changed. In addition, the first arm 19 is rotatable with respect to the carriage unit 14 with a vertical axis as a rotation axis.

The second arm 20 extends in a horizontal direction from a distal end of the first arm 19. The second arm 20 can be expanded and contracted in the horizontal direction. Along with the expansion and contraction of the second arm 20, a horizontal position of the radiation source 15 is changed. The expansion/contraction positions of the first arm 19 and the second arm 20 are detected by a linear encoder, for example.

The radiation source 15 includes a radiation tube 21 and an irradiation field limiter 22. The radiation tube 21 is provided with a filament, a target, a grid electrode, and the like (all of which are not shown). A voltage is applied between the filament, which is a cathode, and the target, which is an anode. The voltage applied between the filament and the target is called a tube voltage. The filament releases thermoelectrons corresponding to the applied tube voltage toward the target. The target emits the radiation R by collision of the thermoelectrons from the filament. The grid electrode is disposed between the filament and the target. The grid electrode changes a flow rate of the thermoelectrons from the filament toward the target in accordance with the applied voltage. The flow rate of the thermoelectrons from the filament toward the target is called a tube current.

The irradiation field limiter 22 is also called a collimeter and limits an irradiation field of the radiation R emitted from the radiation tube 21. The irradiation field limiter 22 has a configuration in which, for example, four shielding plates, such as lead, which shield the radiation R are disposed on respective sides of the quadrangle and an emission opening of the quadrangle that transmits the radiation R is formed in a central portion. The irradiation field limiter 22 changes a size of the emission opening by changing a position of each shielding plate, thereby changing the irradiation field of the radiation R.

A radiation source control device 23 and a tube voltage generator 24 are built in the carriage unit 14. The radiation source control device 23 is wirelessly connected to the console 12 in a communicable manner. The radiation source control device 23 controls an operation of the tube voltage generator 24. In addition, the irradiation switch 16 is connected to the radiation source control device 23. The radiation source control device 23 controls an operation of the radiation source 15 in response to various instruction signals from the irradiation switch 16. The irradiation switch 16 is operated in a case in which the operator OP instructs the radiation source 15 to start the irradiation with the radiation R. The irradiation switch 16 is attachably and detachably attached to the carriage unit 14.

An irradiation condition 63 (see FIG. 5) of the radiation R is set in the radiation source control device 23. The irradiation condition 63 is the tube voltage, the tube current, and the irradiation time of the radiation R applied to the radiation tube 21. In a case in which the instruction to start the irradiation with the radiation R is given by the operation of the irradiation switch 16, the radiation source control device 23 operates the tube voltage generator 24 in accordance with the set irradiation condition 63 to emit the radiation R from the radiation tube 21. The radiation source control device 23 stops the irradiation with the radiation R from the radiation tube 21 in a case in which the irradiation time set in the irradiation condition 63 elapses after the irradiation with the radiation R is started. The tube voltage generator 24 generates the tube voltage by boosting an input voltage with a transformer. The tube voltage generated by the tube voltage generator 24 is supplied to the radiation tube 21 through a voltage cable (not shown).

It should be noted that the irradiation with the radiation R may end by an auto exposure control (AEC) function. The AEC function is a function of detecting the dose of the radiation R during the irradiation with the radiation R, and stopping the irradiation of the radiation R from the radiation tube 21 at a point in time at which a cumulative dose which is an integrated value of the detected dose, reaches a preset target dose.

A cassette storage portion 25 and a handle 26 are provided at a rear portion of the carriage unit 14. The cassette storage portion 25 stores the electronic cassette 11. There are a plurality of types of the electronic cassettes 11 having vertical and horizontal sizes, such as 17 inches×17 inches, 17 inches×14 inches, and 12 inches×10 inches. The cassette storage portion 25 can store a plurality of the electronic cassettes 11 having a plurality of types, regardless of the type. In addition, the cassette storage portion 25 has a function of charging a battery of the stored electronic cassette 11.

The handle 26 is gripped by the operator OP in order to steer the carriage unit 14, and thus the mobile radiation generation device 10. The operator OP causes the mobile radiation generation device 10 to travel while gripping the handle 26.

The console 12 is, for example, a tablet terminal and is an example of an "imaging support apparatus" according to the technology of the present disclosure. It should be noted that the console 12 may be a laptop personal computer or the like.

Figure 3:
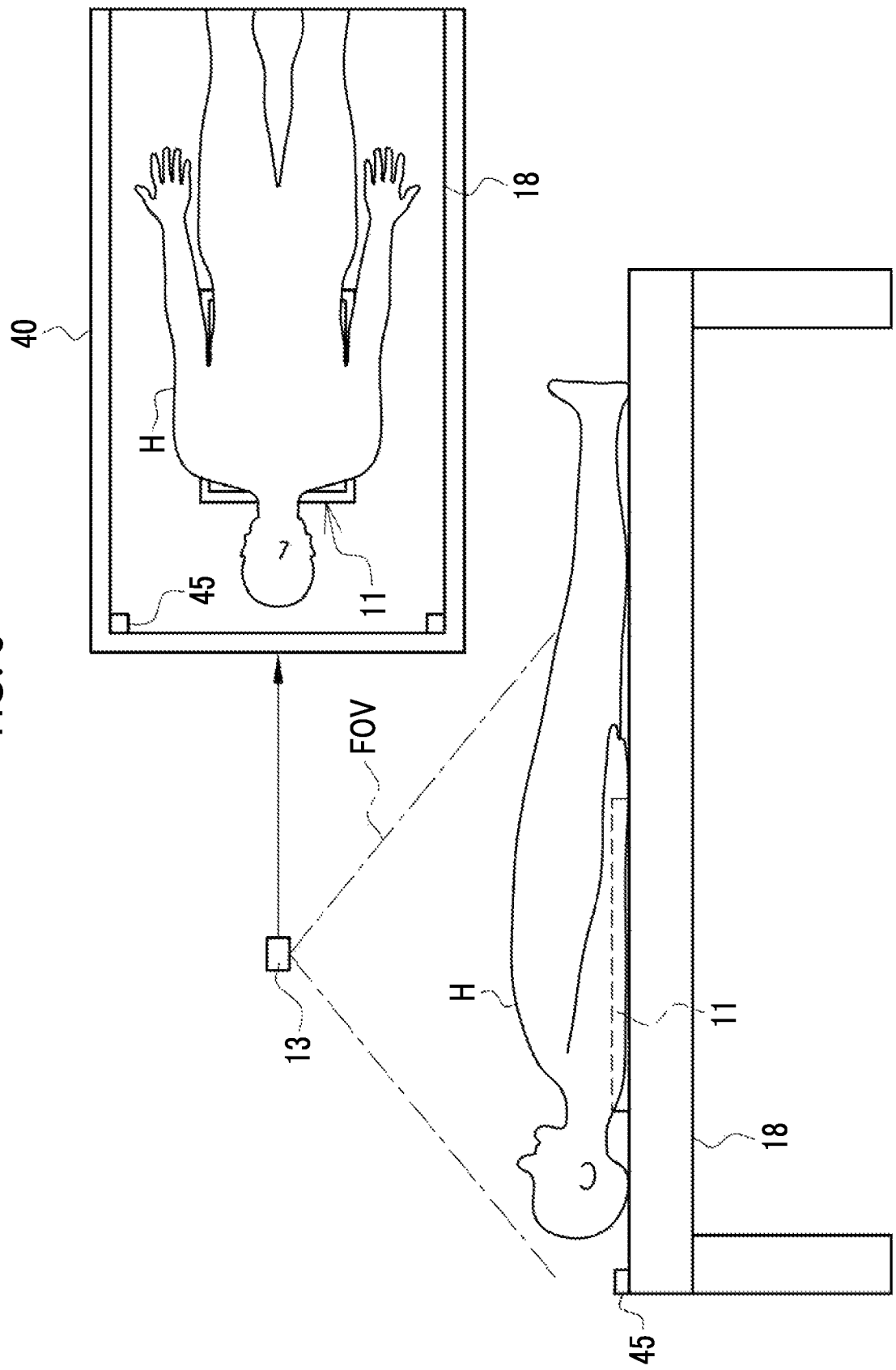
FIG. 3 is a diagram showing a state in which an optical image is captured by a camera.

The camera 13 is a digital camera which captures a digital optical image 40 (see FIG. 3). The camera 13 is attached to the center of a distal end of the irradiation field limiter 22 of the radiation source 15. The camera 13 is wirelessly connected to the console 12 in a communicable manner. The camera 13 images the subject H lying down on the bed 18 in response to an imaging instruction from the console 12. The imaging instruction for the optical image 40 to the camera 13 through the console 12 is, for example, given by the operator OP after the mobile radiation generation device 10 is brought into the hospital room. The camera 13 transmits the captured optical image 40 to the console 12. It should be noted that the camera 13 may be built in the irradiation field limiter 22.

Figure 2:
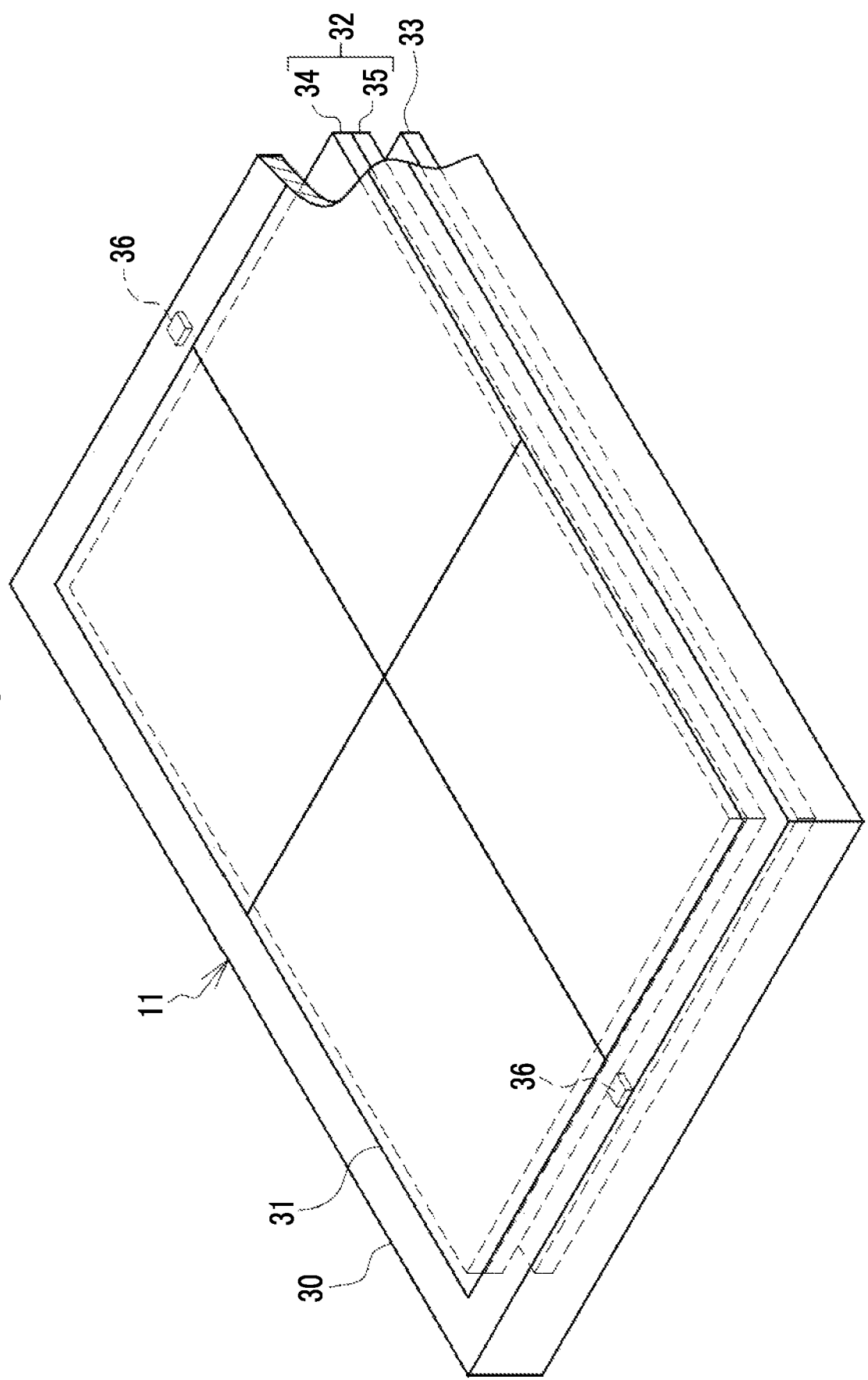
FIG. 2 is a perspective view of an electronic cassette.

As shown in FIG. 2 as an example, the electronic cassette 11 includes a portable housing 30 having a flat box-like shape (rectangular shape in a plan view). The housing 30 is made of metal or resin having conductivity. Therefore, the housing 30 also functions as an electromagnetic shield for preventing electromagnetic noise from entering an inside of the electronic cassette 11 and radiating the electromagnetic noise from the electronic cassette 11 to an outside. A rectangular plate-shaped radiation transmission plate 31 that is one size smaller than the housing 30 is attached to a front surface of the housing 30 on which the radiation R is incident. The radiation transmission plate 31 is made of, for example, a carbon material that is lightweight, has high rigidity, and has high radiation transmittance.

An image detection unit 32 and a circuit unit 33 are built in the housing 30. The image detection unit 32 is composed of a scintillator 34 and a detection panel 35 having substantially the same size as the radiation transmission plate 31. The scintillator 34 and the detection panel 35 are laminated in an order of the scintillator 34 and the detection panel 35 as viewed from a front surface side of the housing 30 on which the radiation R is incident.

The scintillator 34 has a phosphor, such as thallium-activated cesium iodide (CsI:Tl) or terbium-activated gadolinium oxysulfide ($Gd_2O_2S$:Tb, GOS), and converts the incident radiation R into visible light and releases the visible light. The detection panel 35 has a configuration in which a plurality of pixels are arranged in a two-dimensional matrix on one thin film transistor (TFT) active matrix substrate. A substantially entire surface of the surface of the detection panel 35 functions as a detection region DR (see FIG. 4) of the radiation R. The detection panel 35 accumulates the charge corresponding to the visible light released from the scintillator 34 in the pixel, converts the charge accumulated in the pixel into an electric signal, and outputs the electric signal. The detection panel 35 is also called a flat panel detector (FPD).

The circuit unit 33 controls an operation of the detection panel 35. Specifically, in a case in which the irradiation with the radiation R is started, the circuit unit 33 causes the detection panel 35 to perform an accumulation operation of accumulating the charge in the pixels. In addition, in a case in which the irradiation with the radiation R ends, the circuit unit 33 causes the detection panel 35 to perform a readout operation of reading out the charge accumulated in the pixels as the electric signal. In a case in which the irradiation with the radiation R ends by the AEC function, the circuit unit 33 causes the detection panel 35 to perform the readout operation in a case in which the cumulative dose of the radiation R reaches the target dose. The circuit unit 33 generates a radiation image 66 based on the electric signal output from the detection panel 35.

Two radio wave receivers 36 are attached to the inside of the housing 30 at symmetrical positions at the center of the upper and lower sides. The radio wave receiver 36 is provided to detect a position of the electronic cassette 11 on the bed 18. That is, the radio wave receiver 36 is an example of a "position detection sensor" according to the technology of the present disclosure.

The scintillator 34 and the detection panel 35 may be laminated in an order of the detection panel 35 and the scintillator 34 as viewed from the front surface side. In addition, the image detection unit 32 may be a direct conversion type that directly converts the radiation R into the electric signal instead of an indirect conversion type that converts the radiation R as the visible light by the scintillator 34 of the present example into the electric signal by the detection panel 35.

Although not shown, the housing 30 includes a battery and an antenna which are built therein. The electronic cassette 11 can perform wireless communication with the console 12 by the antenna. In a case in which wireless communication is performed with the console 12, the electronic cassette 11 is driven by electric power from the battery and can be used wirelessly.

FIG. 3 shows an example of a state in which the camera 13 images the subject H lying down on the bed 18 for the chest portion front surface imaging in response to the imaging instruction of the operator OP. In this case, the radiation source 15, and thus the camera 13, are positioned directly above the chest portion of the subject H. At this position, the camera 13 has a field of view FOV capable of imaging about ¾ of the bed 18, an upper body of the subject H lying down on the bed 18, and a part of a lower body up to below the knee. The optical image 40 captured by the camera 13 in this way shows about ¾ of the bed 18, the upper body of the subject H lying down on the bed 18, and a part of the lower body up to below the knee.

Here, the object "shown" in the optical image 40 includes an object that is present in the optical image 40 but is covered and hidden by some object. Therefore, the electronic cassette 11 that is inserted between the subject H and the bed 18 and is covered and hidden by the subject H can also be referred to as the object "shown" in the optical image 40.

Figure 4:
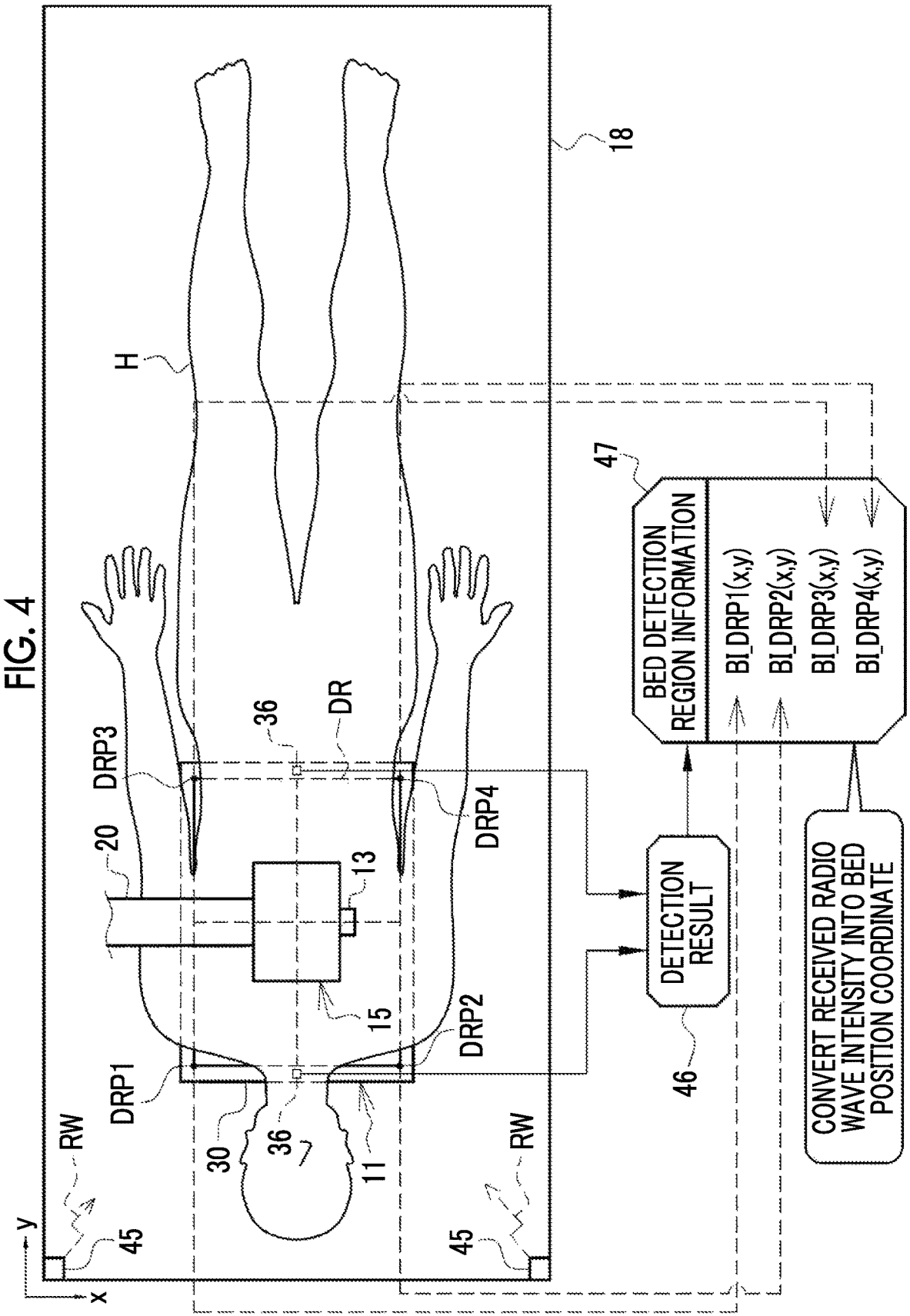
FIG. 4 is a view of a radiation source, a subject, the electronic cassette, and a bed as viewed from above.

As an example, as shown in FIG. 4, two radio wave transmitters 45 are installed by the operator OP at two corners of the bed 18 on a head portion side of the subject H. The two radio wave transmitters 45 transmit radio waves RW toward the radio wave receivers 36 of the electronic cassette 11. The radio wave RW has the same intensity in each radio wave transmitter 45, but has a different frequency. That is, the radio wave RW has two channels. The radio wave receiver 36 receives the radio wave RW of each of the two channels. The radio wave receiver 36 outputs the intensity of the received radio wave RW of the two channels (hereinafter, referred to as the received radio wave intensity) as a detection result 46.

The received radio wave intensity is changed in accordance with a distance from the radio wave transmitter 45 to the radio wave receiver 36. Therefore, the distance from the radio wave transmitter 45 to the radio wave receiver 36 can be grasped from the received radio wave intensity. In a case in which the distance from the radio wave transmitter 45 to the radio wave receiver 36 is grasped, the position of the electronic cassette 11 on the bed 18 can also be grasped. In addition, a positional relationship between the radio wave receiver 36 and four vertexes DRP1, DRP2, DRP3, and DRP4 of the detection region DR is known. Therefore, bed detection region information 47 indicating the positions of the vertexes DRP1 to DRP4 can be derived from the detection result 46. The electronic cassette 11 transmits the bed detection region information 47 to the console 12.

The bed detection region information 47 is a bed position coordinate BI_DRP1 (x, y) of the vertex DRP1, a bed position coordinate BI_DRP2 (x, y) of the vertex DRP2, a bed position coordinate BI_DRP3 (x, y) of the vertex DRP3, and a bed position coordinate BI_DRP4 (x, y) of the vertex DRP4. The bed position coordinate BI (x, y) is a position coordinate in a case in which, for example, an installation position of the radio wave transmitter 45 on the left side of the subject H among the two radio wave transmitters 45 is set as an origin and a direction along a short side of the bed 18 is set as an x-axis and a direction along a long side of the bed 18 is set as an y-axis. It should be noted that the bed position coordinate BI (x, y) of a diagonal point of the detection region DR, such as the bed position coordinate BI_DRP1 (x, y) and the bed position coordinate BI_DRP4 (x, y), may be set as the bed detection region information 47.

Figure 5:
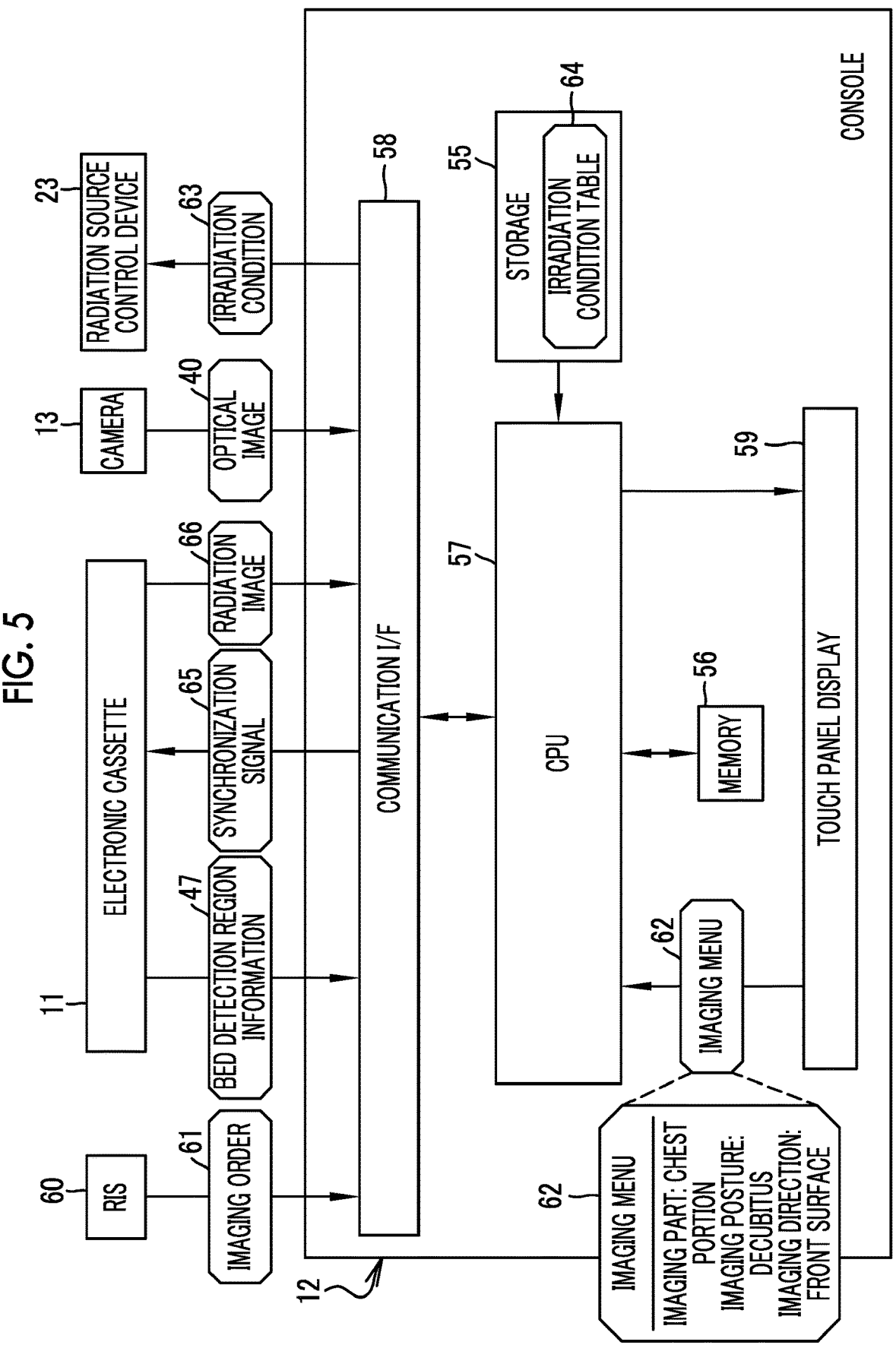
FIG. 5 is a block diagram showing a configuration of a console.

As shown in FIG. 5 as an example, the console 12 comprises a storage 55, a memory 56, a central processing unit (CPU) 57, a communication interface (I/F) 58, and a touch panel display 59. The storage 55, the memory 56, the CPU 57, the communication I/F 58, and the touch panel display 59 are connected to each other via a busline (not shown). The storage 55, the memory 56, the CPU 57, and the busline are examples of a "computer" according to the technology of the present disclosure.

The storage 55 is a hard disk drive built in a computer constituting the console 12 or a hard disk drive connected to the computer through a cable or a network. In the storage 55, a control program, such as an operating system, various application programs, various data associated with such programs, and the like are stored. It should be noted that a solid state drive may be used instead of the hard disk drive.

The memory 56 is a work memory for the CPU 57 to execute processing. The CPU 57 loads the program stored in the storage 55 into the memory 56 and executes the processing in accordance with the program. As a result, the CPU 57 controls each unit of the computer in an integrated manner. The CPU 57 is an example of a "processor" according to the technology of the present disclosure. It should be noted that the memory 56 may be built in the CPU 57.

The communication I/F 58 controls transmission of various types of information with an external device, such as the electronic cassette 11. The touch panel display 59 displays various screens and receives an operation instruction from the operator OP. The touch panel display 59 is an example of a "display" according to the technology of the present disclosure.

The CPU 57 receives an imaging order 61 from the radiology information system (RIS) 60 via the communication I/F 58. In the imaging order 61, a subject identification data (ID) for identifying the subject H, an instruction of an imaging technique by a doctor or the like of a medical department who has issued the imaging order 61, and the like are registered. The CPU 57 displays the imaging order 61 on the touch panel display 59 in response to an instruction from the operator OP through the touch panel display 59. The operator OP confirms a content of the imaging order 61 through the touch panel display 59.

The CPU 57 displays a plurality of types of imaging menus 62 on the touch panel display 59 in a manner in which a plurality of types of imaging menus 62 can be selected. The imaging menu 62 defines an imaging technique in which an imaging part of the subject H, an imaging posture of the subject H, and an imaging direction of the subject H are set as one set, such as "chest portion, decubitus, front surface". The imaging part includes a head portion, a neck portion, an abdomen portion, a waist portion, a shoulder, an elbow, a hand, a knee, an ankle, and the like, in addition to the chest portion. The imaging posture includes upright, sitting, and the like, in addition to the decubitus. The imaging direction includes a back surface, a side surface, and the like, in addition to the front surface. The operator OP operates the touch panel display 59 to select one imaging menu 62 that matches the imaging technique designated in the imaging order 61 from among the plurality of types of imaging menus 62. As a result, the CPU 57 receives the imaging menu 62. The CPU 57 reads out the irradiation condition 63 corresponding to the received imaging menu 62 from an irradiation condition table 64 stored in the storage 55. The CPU 57 displays the read out irradiation condition 63 on the touch panel display 59. In the irradiation condition table 64, the irradiation conditions 63 corresponding to the various imaging menus 62 are registered. As described above, the irradiation condition 63 is the tube voltage and the tube current applied to the radiation tube 21, and the irradiation time of the radiation R. Instead of the tube current and the irradiation time, a tube current irradiation time product may be set as the irradiation condition 63.

The CPU 57 transmits the set irradiation condition 63 to the radiation source control device 23 via the communication I/F 58. In addition, although not shown, in a case in which the radiation source control device 23 is instructed to start the irradiation with the radiation R through the irradiation switch 16, the CPU 57 receives an irradiation start signal indicating that the irradiation with the radiation R is started from the radiation source control device 23. In a case in which the irradiation start signal is received, the CPU 57 transmits a synchronization signal 65 indicating that the irradiation with the radiation R is started to the electronic cassette 11. Further, the CPU 57 receives an irradiation end signal indicating that the irradiation with the radiation R ends from the radiation source control device 23. In a case in which the irradiation end signal is received, the CPU 57 transmits the synchronization signal 65 indicating that the irradiation with the radiation R ends to the electronic cassette 11.

In a case in which the synchronization signal 65 indicating that the irradiation with the radiation R is started is received from the console 12, the electronic cassette 11 causes the detection panel 35 to start the accumulation operation. In addition, in a case in which the synchronization signal 65 indicating that the irradiation with the radiation R ends is received from the console 12, the electronic cassette 11 causes the detection panel 35 to start the readout operation. It should be noted that the electronic cassette 11 may be provided with a function of detecting the start of the irradiation with the radiation R and the end of the irradiation with the radiation R, the detection panel 35 may be caused to start the accumulation operation in a case in which the start of the irradiation with the radiation R is detected by this function, and the detection panel 35 may be caused to start the readout operation in a case in which the end of the irradiation with the radiation R is detected.

The CPU 57 receives the radiation image 66 from the electronic cassette 11 via the communication I/F 58. The CPU 57 performs various types of image processing on the radiation image 66, and then displays the radiation image 66 on the touch panel display 59 and provides the radiation image 66 for viewing by the operator.

In addition, although not shown, the CPU 57 transmits the imaging instruction to the camera 13 via the communication I/F 58. The CPU 57 receives the optical image 40 captured by the camera 13 in response to the imaging instruction.

Figure 6:
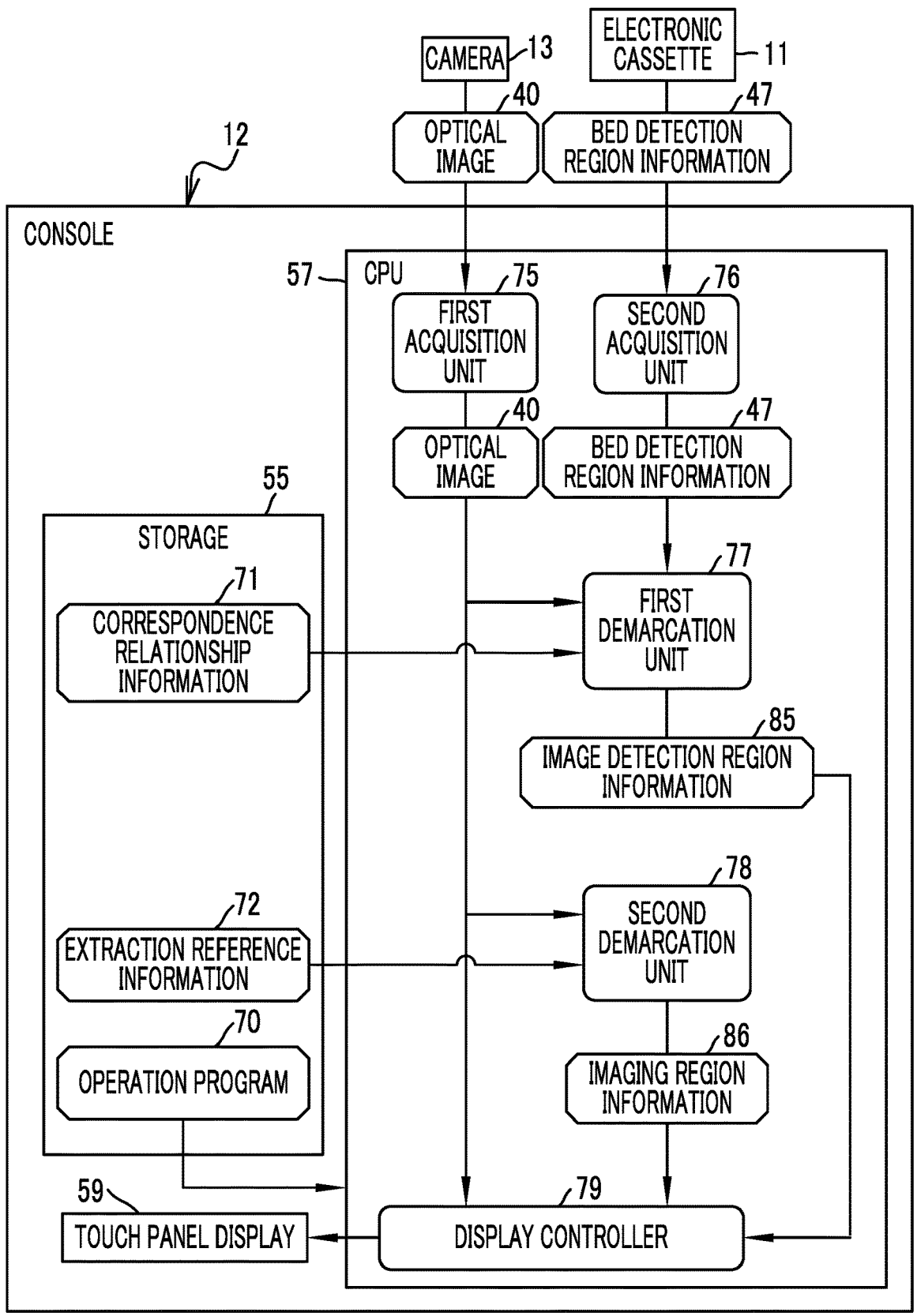
FIG. 6 is a block diagram showing a processing unit of a CPU of the console.

As an example, as shown in FIG. 6, an operation program 70 is stored in the storage 55. The operation program 70 is an application program causing the computer to function as the imaging support apparatus. That is, the operation program 70 is an example of an "operation program of an imaging support apparatus" according to the technology of the present disclosure. Correspondence relationship information 71, extraction reference information 72, and the like are also stored in the storage 55.

In a case in which the operation program 70 is activated, the CPU 57 cooperates with the memory 56 and the like to function as a first acquisition unit 75, a second acquisition unit 76, a first demarcation unit 77, a second demarcation unit 78, and a display controller 79.

The first acquisition unit 75 sequentially acquires the optical images 40 output from the camera 13 at a predetermined frame rate. The first acquisition unit 75 outputs the optical image 40 to the first demarcation unit 77, the second demarcation unit 78, and the display controller 79. The second acquisition unit 76 acquires the bed detection region information 47 from the electronic cassette 11. The second acquisition unit 76 outputs the bed detection region information 47 to the first demarcation unit 77.

The first demarcation unit 77 demarcates the detection region DR in the optical image 40 based on the bed detection region information 47 and the correspondence relationship information 71. The first demarcation unit 77 outputs image detection region information 85, which is information of the demarcated detection region DR, to the display controller 79.

The second demarcation unit 78 demarcates an imaging region IR (see FIG. 10), which is a region to be imaged by the radiography, in the optical image 40 based on the extraction reference information 72. The imaging region IR is a region preset in accordance with the imaging menu 62, and is a region of a human body that should be included in the radiation image 66 in the imaging menu 62. The second demarcation unit 78 outputs imaging region information 86, which is information of the demarcated imaging region IR, to the display controller 79.

The display controller 79 performs control of displaying various screens on the touch panel display 59. The various screens include a display screen of the imaging order 61, a selection screen of the imaging menu 62, an information display screen 95 (see FIGS. 11 to 13), and the like. It should be noted that, although not shown, in the CPU 57, in addition to the processing units 75 to 79, a reception unit that receives the imaging order 61 from the RIS 60, an image processing unit that performs various types of image processing on the radiation image 66, a setting unit that sets the irradiation condition 63 in the radiation source control device 23, and the like are constructed.

In the following, a case of chest portion decubitus front surface imaging will be described as an example.

Figure 7:
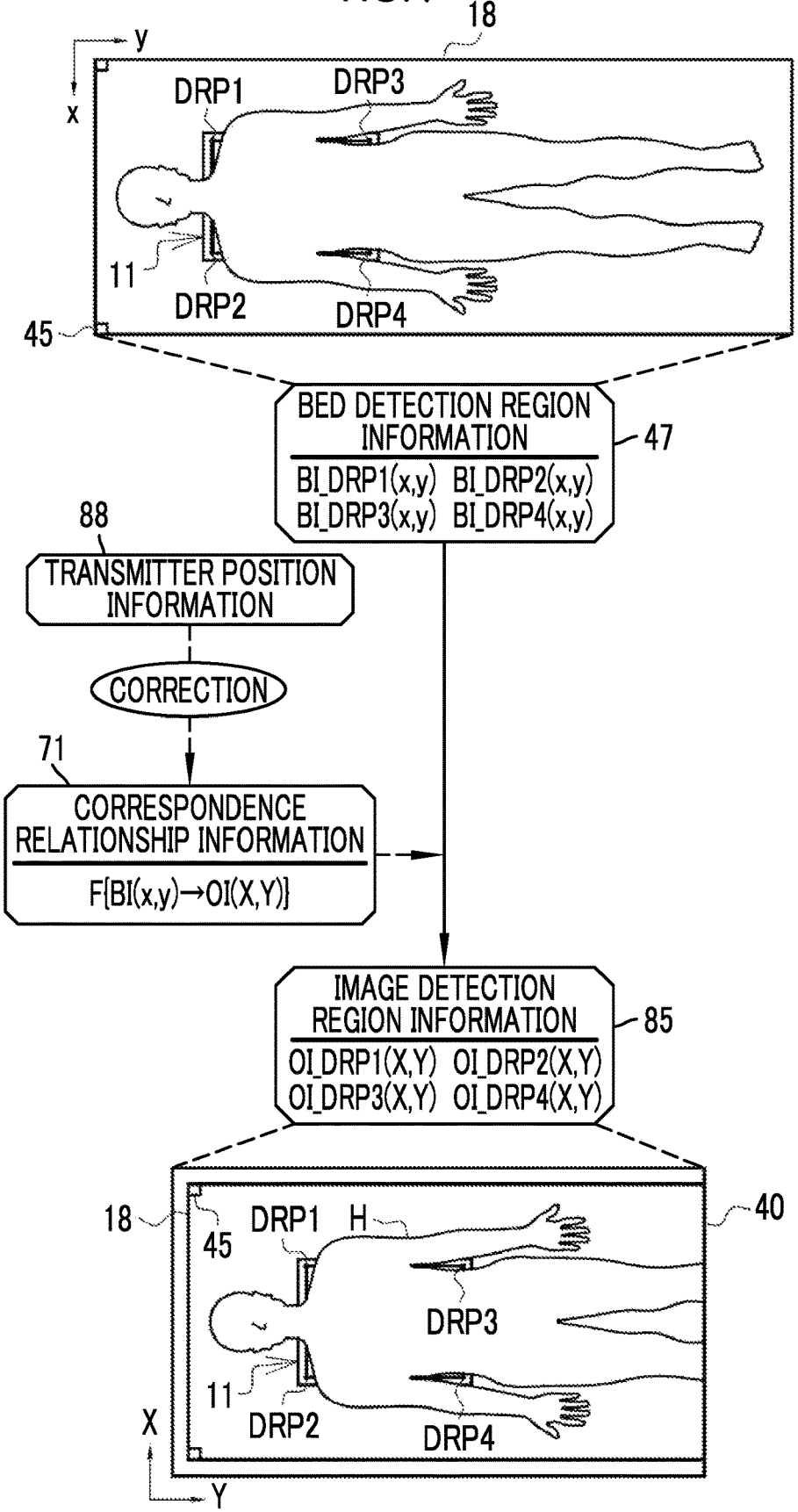
FIG. 7 is a diagram showing processing of a first demarcation unit.

As shown in FIG. 7 as an example, the correspondence relationship information 71 includes a function F for converting the bed position coordinate BI (x, y) into the position coordinate OI (X, Y) of the optical image 40. The first demarcation unit 77 uses the function F to convert the bed position coordinates BI_DRP1 (x, y) to BI_DRP4 (x, y) of the four vertexes DRP1 to DRP4 of the detection region DR of the bed detection region information 47 the position coordinates OI_DRP1 (X, Y), OI_DRP2 (X, Y), OI_DRP3 (X, Y), and OI_DRP4 (X, Y) of the optical image 40 to obtain the image detection region information 85. It should be noted that an origin of the position coordinates OI (X, Y) of the optical image 40 is, for example, a left end of the optical image 40, an X-axis is a direction along the short side of the optical image 40, and a Y-axis is a direction along the long side of the optical image 40.

The first demarcation unit 77 corrects the function F of the correspondence relationship information 71 by transmitter position information 88. The transmitter position information 88 is obtained by performing image recognition on the radio wave transmitter 45 shown in the optical image 40. The transmitter position information 88 is specifically the position coordinate OI (X, Y) of the radio wave transmitter 45 in the optical image 40 and the size of the radio wave transmitter 45. The position and the size of the radio wave transmitter 45 in the optical image 40 is changed in accordance with a position of the camera 13 with respect to the bed 18. Therefore, the transmitter position information 88 can be referred to as information indicating a positional relationship between the camera 13 and the bed 18. The radio wave transmitter 45 functions as a marker for recognizing the position of the camera 13 with respect to the bed 18, in addition to transmitting the radio waves RW.

Figure 8:
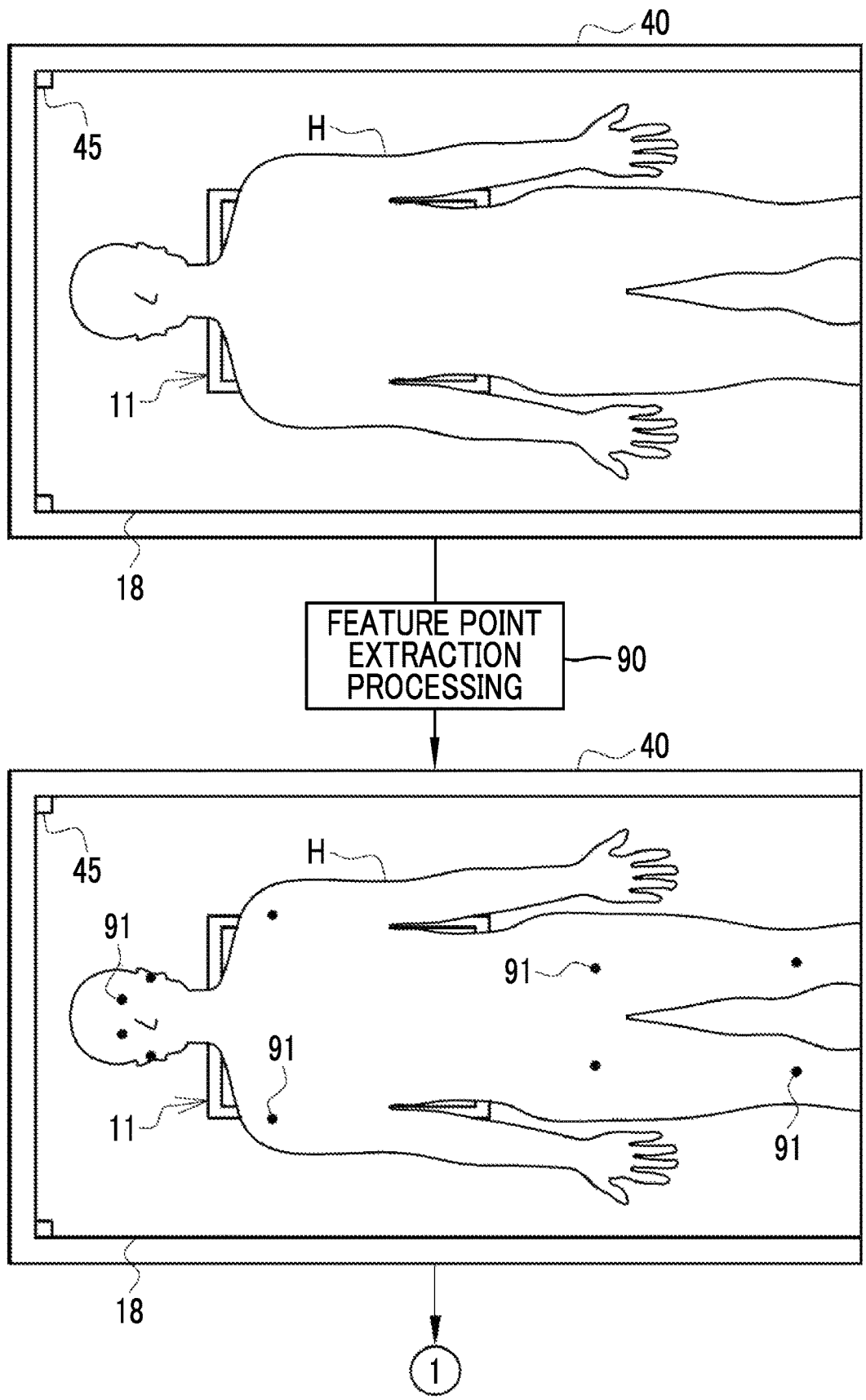
FIG. 8 is a diagram showing processing of a second demarcation unit.

As shown in FIG. 8 as an example, the second demarcation unit 78 performs feature point extraction processing 90 on the optical image 40. The feature point extraction processing 90 is processing of extracting a feature point 91 of the subject H shown in the optical image 40 by using a well-known image recognition technology or a machine learning model. From the top, the feature points 91 are right and left orbital points, right and left external auditory canal points, right and left shoulder joint points, right and left hip joint points, and right and left knee joint points. As is well known, an orbit is a depression in which an eyeball is accommodated, and the orbital point is a center point of the depression. An external auditory canal is a so-called ear canal, and the external auditory canal point is a center point of the ear canal. The shoulder joint point is a connection point between a shoulder blade and a humerus. The hip joint point is a connection point between a hip bone and a femoral bone. The knee joint point is a connection point between the femoral bone and a shinbone.

Figure 9:
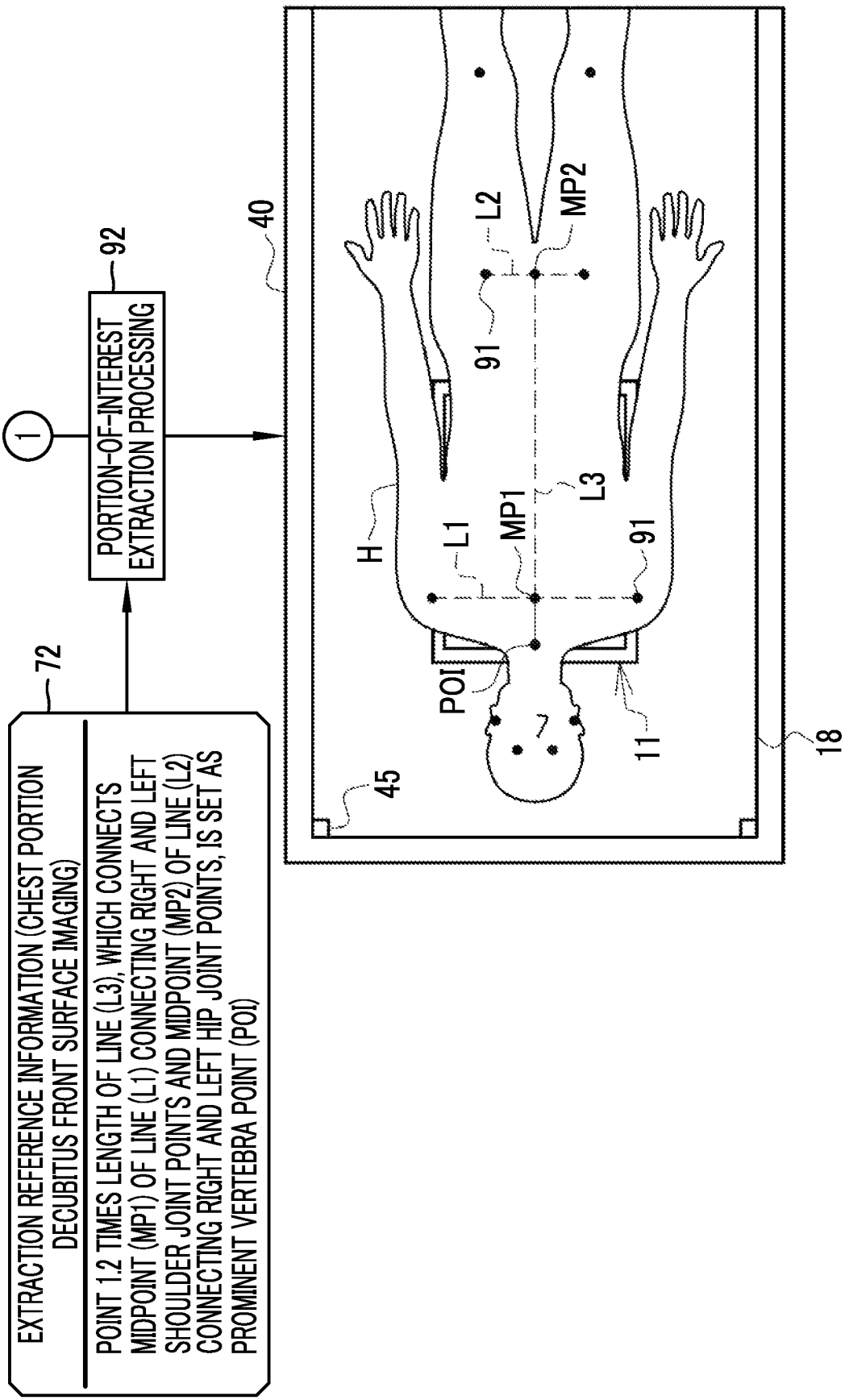
FIG. 9 is a diagram showing the processing of the second demarcation unit.

As shown in FIG. 9 as an example, the second demarcation unit 78 performs the feature point extraction processing 90 and then portion-of-interest extraction processing 92 on the optical image 40. The portion-of-interest extraction processing 92 is processing of extracting a portion of interest POI from the feature point 91 with reference to the extraction reference information 72. The portion of interest POI in the present example is a center point of the prominent vertebra (hereinafter, referred to as a prominent vertebra point). Therefore, the extraction reference information 72 is information for specifying the prominent vertebra. Specifically, the extraction reference information 72 is a content in which a point 1.2 times a length of the line L3, which connects a midpoint MP1 of the line L1 connecting the right and left shoulder joint points and a midpoint MP2 of the line L2 connecting the right and left hip joint points, is set as the prominent vertebra point. Therefore, a length of a line connecting the midpoint MP2 and the prominent vertebra point is 1.2 times the length of the line L3.

It should be noted that the numerical value of "1.2 times" of the extraction reference information 72 is statistically obtained from the data of a large number of unspecified subjects H in the past. For example, the numerical values may be changed in accordance with the attribute of the subject H, such as gender, age, and body type, such as 1.2 times for men, 1.18 times for women, 1.12 times for children, and 1.22 times for height of 180 cm or more.

Figure 10:
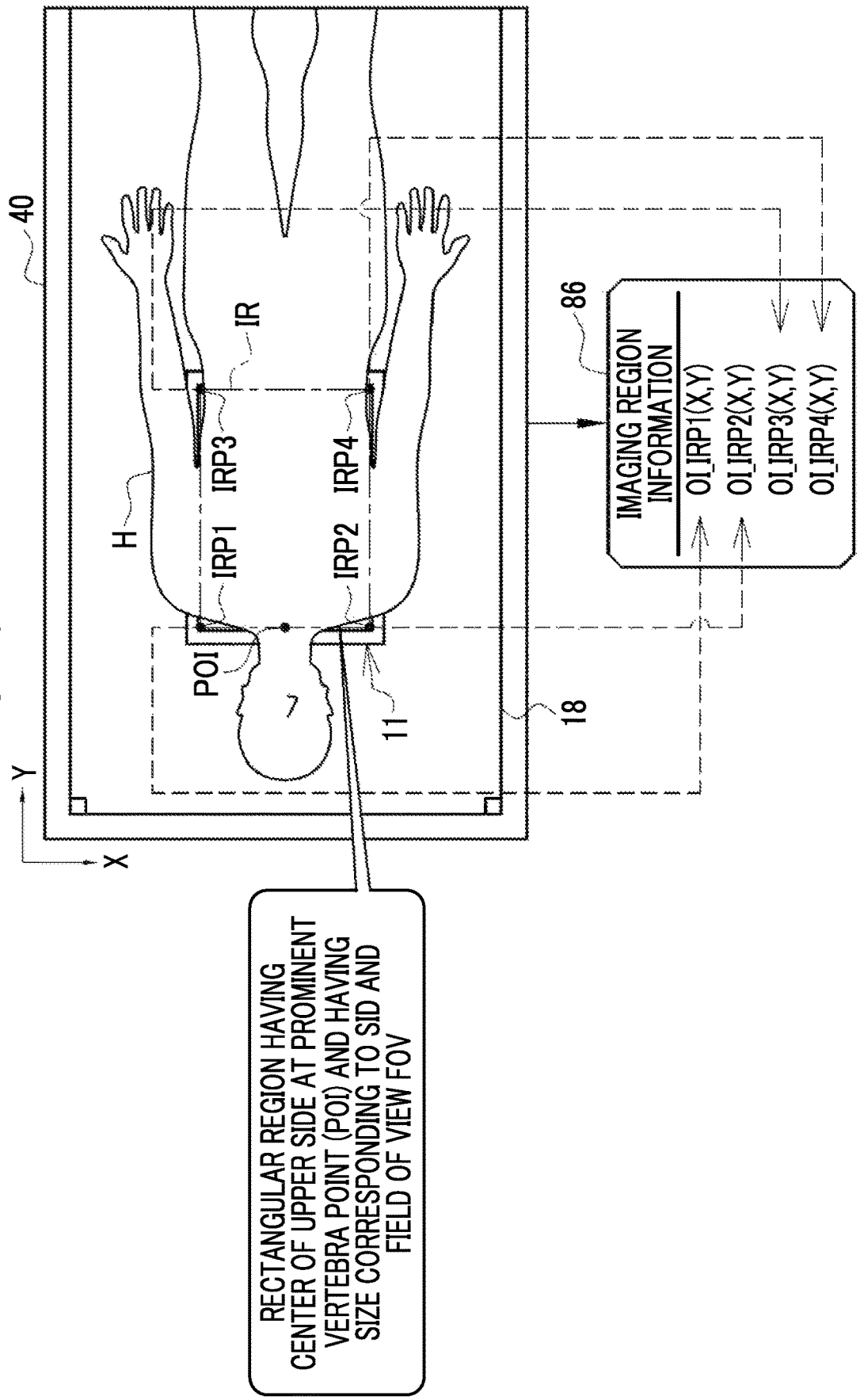
FIG. 10 is a diagram showing the processing of the second demarcation unit.

As shown in FIG. 10 as an example, the second demarcation unit 78 demarcates a rectangular region which has a center of the upper side at the prominent vertebra point, the rectangular region having a size corresponding to a source to image receptor distance (SID) and the field of view FOV of the camera 13, as the imaging region IR. As is well known, the SID is a distance from a generation point of the radiation R to the surface of the detection panel 35. The SID can be obtained from the size of the radio wave transmitter 45 shown in the optical image 40. The second demarcation unit 78 outputs the position coordinates OI_IRP1 (X, Y), OI_IRP2 (X, Y), OI_IRP3 (X, Y), and OI_IRP4 (X, Y) of the four vertexes IRP1, IRP2, IRP3, and IRP4 of the imaging region IR to the display controller 79, as the imaging region information 86. It should be noted that, even in the position coordinate OI (X, Y) of the diagonal point of the imaging region IR, such as the position coordinate OI_IRP1 (X, Y) and the position coordinate OI_IRP4 (X, Y), may be output as the imaging region information 86.

Figure 11:
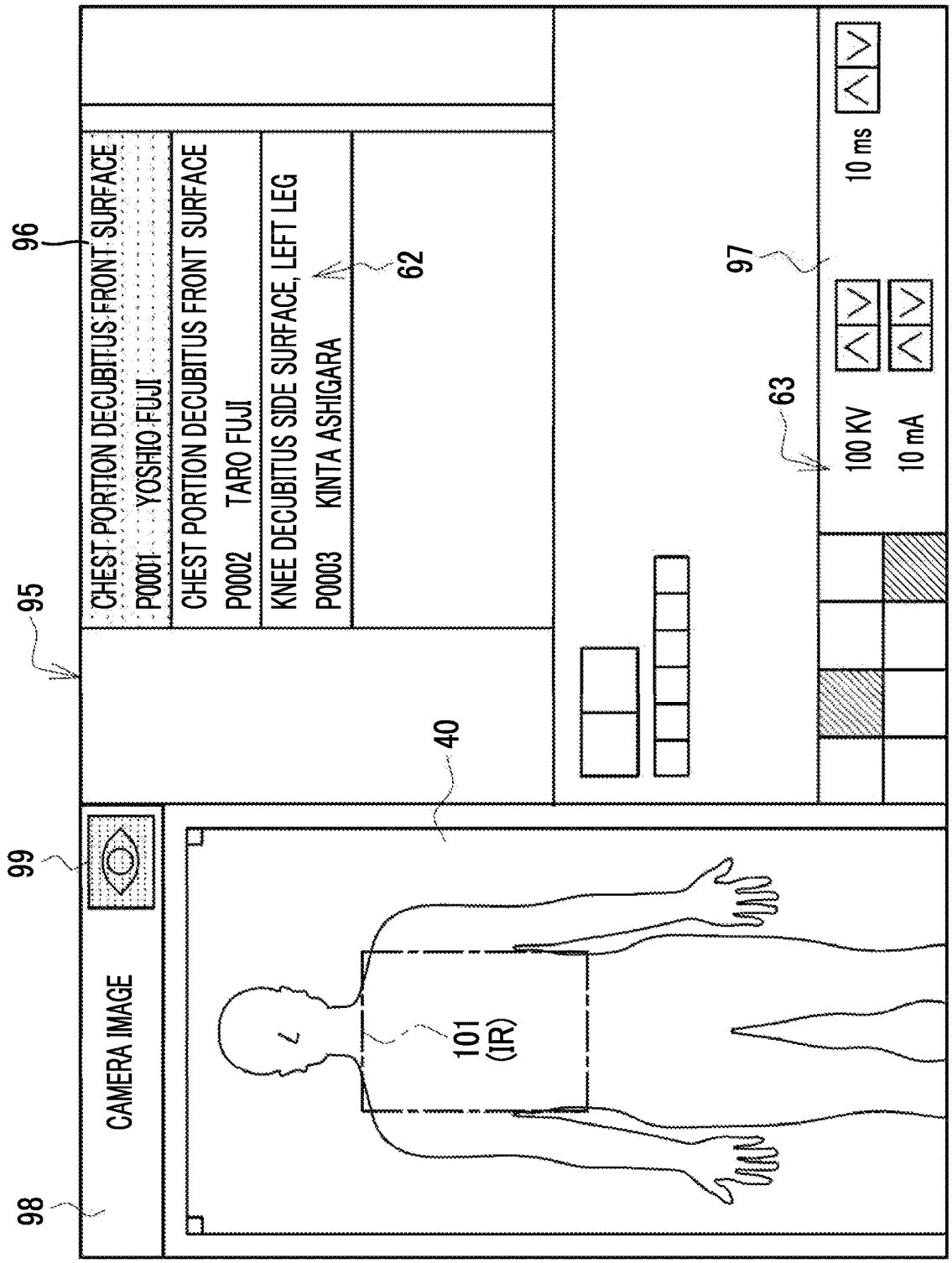
FIG. 11 is a diagram showing an information display screen before the electronic cassette is inserted between the subject and the bed.
Figure 12:
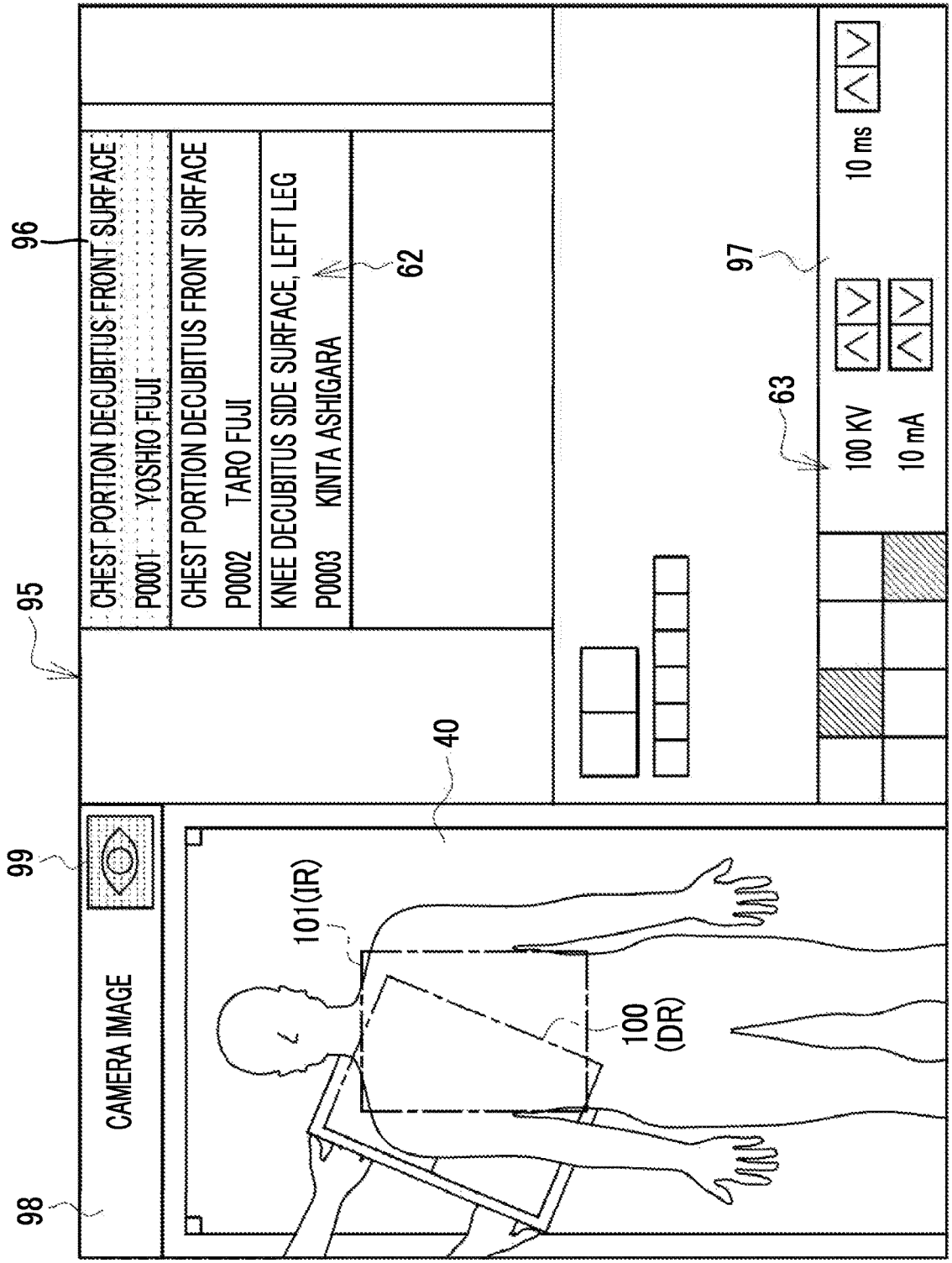
FIG. 12 is a diagram showing the information display screen during the insertion of the electronic cassette between the subject and the bed.
Figure 13:
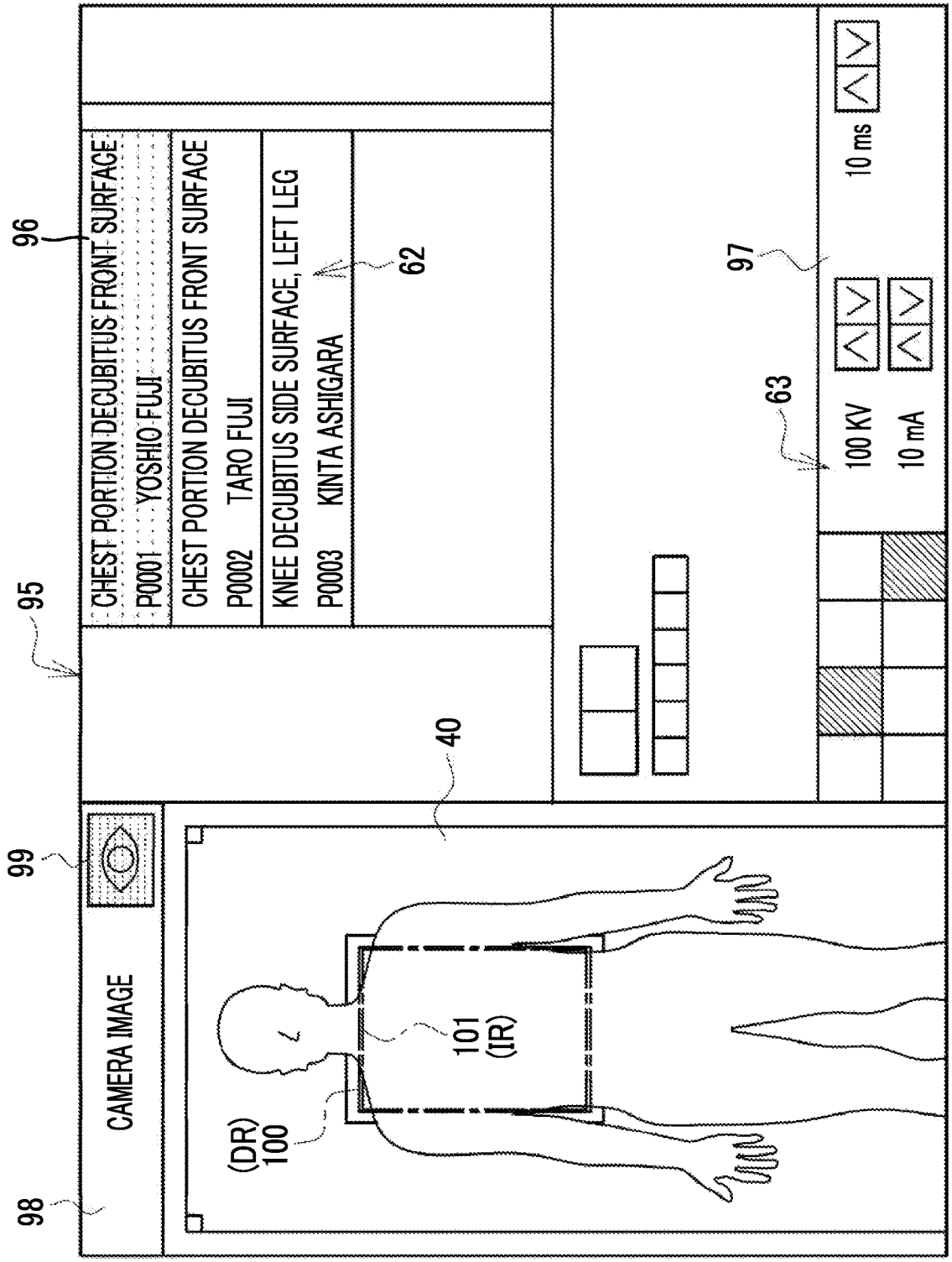
FIG. 13 is a diagram showing the information display screen in a case in which the insertion of the electronic cassette between the subject and the bed ends.

As shown in FIGS. 11 to 13 as an example, the information display screen 95 includes a display region 96 of the imaging menu 62 and a display region 97 of the irradiation condition 63. In the display region 96, a set of the imaging menu 62, the subject ID, and the name of the subject H registered so far is displayed side by side. The imaging menu 62 of the currently performed radiography is displayed in a color different from that of the other imaging menus 62, as indicated by hatching. The display region 97 displays the tube voltage, the tube current, and the irradiation time under the irradiation condition 63 in an adjustable state.

The information display screen 95 also includes a display region 98 of the optical image 40. An imaging instruction button 99 is provided on the upper portion of the display region 98. The imaging instruction button 99 is a turning on/off button. In a state in which the imaging instruction button 99 is turned off, the imaging instruction for the optical image 40 is not transmitted to the camera 13. Therefore, the optical image 40 is not displayed in the display region 98. On the other hand, in a case in which the imaging instruction button 99 is turned on, the imaging instruction for the optical image 40 is transmitted to the camera 13, so that the optical image 40 is displayed in the display region 98. The display controller 79 displays the optical images 40 output from the camera 13 at a predetermined frame rate in the display region 98 while sequentially updating the optical images 40. That is, the optical image 40 displayed in the display region 98 is a live view image (moving image).

The display controller 79 displays a frame 100 indicating the detection region DR on the optical image 40 of the display region 98 in a superimposed manner based on the image detection region information 85. In addition, the display controller 79 displays a frame 101 indicating the imaging region IR on the optical image 40 of the display region 98 in a superimposed manner based on the imaging region information 86. It should be noted that the frame 100 is an example of an "indicator indicating the detection region" according to the technology of the present disclosure. In addition, the frame 101 is an example of an "indicator indicating an imaging region" according to the technology of the present disclosure.

FIG. 11 shows the information display screen 95 before the electronic cassette 11 is inserted between the subject H and the bed 18. In this case, the subject H is shown in the optical image 40, whereas the electronic cassette 11 is not shown in the optical image 40. Therefore, only the frame 101 indicating the imaging region IR is displayed on the optical image 40 of the display region 98 in a superimposed manner.

FIG. 12 shows the information display screen 95 during the insertion of the electronic cassette 11 between the subject H and the bed 18. In this case, the optical image 40 also shows the electronic cassette 11 in addition to the subject H. Therefore, in addition to the frame 101 indicating the imaging region IR, the frame 100 indicating the detection region DR is also displayed on the optical image 40 of the display region 98 in a superimposed manner.

FIG. 13 shows the information display screen 95 in a case in which the insertion of the electronic cassette 11 between the subject H and the bed 18 ends. In this case as well, as in the case of FIG. 12, the frame 100 indicating the detection region DR and the frame 101 indicating the imaging region IR are displayed on the optical image 40 in the display region 98 in a superimposed manner.

Figure 14:
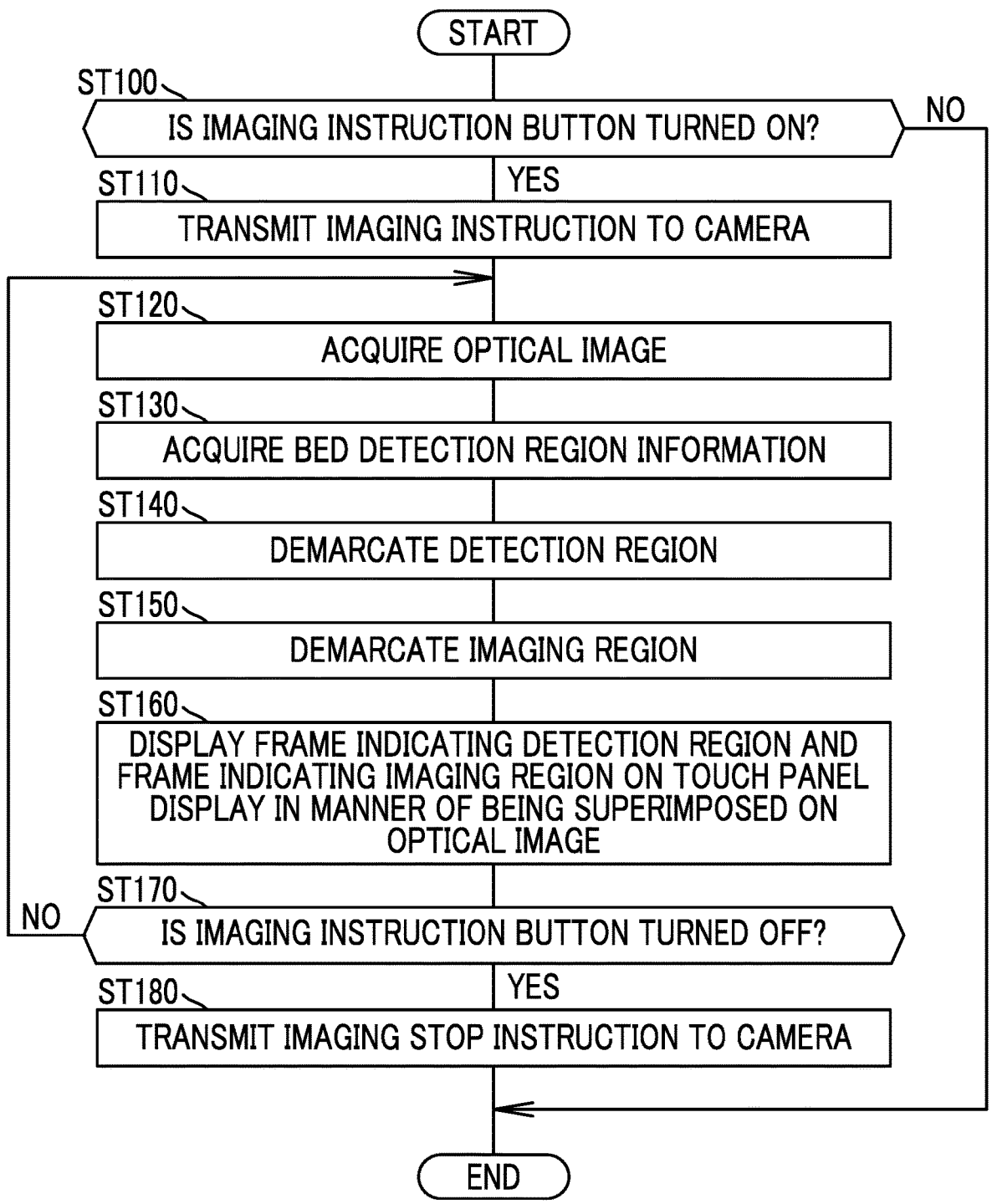
FIG. 14 is a flowchart showing a processing procedure of the console.

Next, an action with the configuration described above will be described with reference to the flowchart shown in FIG. 14 as an example. Prior to the radiography, the operator performs imaging preparation work. The imaging preparation work includes selection of the imaging menu 62, setting of the irradiation condition 63 of the radiation R, installation of the radio wave transmitter 45 on the bed 18, position adjustment of the subject H on the bed 18, position adjustment of the radiation source 15 with respect to the bed 18 (adjustment of the horizontal position and the SID), the size adjustment of the irradiation field, the position adjustment of the electronic cassette 11, and the like.

In the console 12, the operation program 70 is activated, so that the CPU 57 functions as the first acquisition unit 75, the second acquisition unit 76, the first demarcation unit 77, the second demarcation unit 78, and the display controller 79.

The operator OP operates the console 12 to select the imaging menu 62 in accordance with the radiography to be performed, and then sets the irradiation condition 63 for the radiation R. The operator OP installs the radio wave transmitter 45 at each of the two corners of the bed 18 on the head portion side of the subject H. Thereafter, the operator OP performs the position adjustment of the subject H such that the head-caudal direction is parallel to the long side direction of the bed 18.

The operator OP expands and contracts the first arm 19 and the second arm 20 to perform the position adjustment of the radiation source 15 with respect to the bed 18. In addition, the operator OP operates the irradiation field limiter 22 to perform the size adjustment of the irradiation field.

Before inserting the electronic cassette 11 between the subject H and the bed 18, the operator OP turns on the imaging instruction button 99 on the information display screen 95 to issue the imaging instruction for the optical image 40 (YES in step ST100). The imaging instruction is transmitted to the camera 13 from the console 12 (step ST110). As a result, as shown in FIG. 3, the optical image 40 is captured by the camera 13.

The optical image 40 from the camera 13 is acquired by the first acquisition unit 75 (step ST120). The optical image 40 is output to the first demarcation unit 77, the second demarcation unit 78, and the display controller 79 from the first acquisition unit 75.

In addition, as shown in FIG. 4, in a case in which an attempt is made to insert the electronic cassette 11 between the subject H and the bed 18, the radio wave RW from the radio wave transmitter 45 is received by the radio wave receiver 36 of the electronic cassette 11, and the received radio wave intensity thereof is output as the detection result 46. In the electronic cassette 11, based on the detection result 46, the bed detection region information 47, which includes the bed position coordinates BI_DRP1 (x, y) to BI_DRP4 (x, y) of the four vertexes DRP1 to DRP4 of the detection region DR of the radiation R by the detection panel 35, is derived.

The bed detection region information 47 from the electronic cassette 11 is acquired by the second acquisition unit 76 (step ST130). The bed detection region information 47 is output to the first demarcation unit 77 from the second acquisition unit 76. It should be noted that, in a case in which the electronic cassette 11 is at a position at which the radio wave RW from the radio wave transmitter 45 cannot be received, step ST130 is omitted.

As shown in FIG. 7, in the first demarcation unit 77, the image detection region information 85 is derived from the bed detection region information 47 by using the correspondence relationship information 71. As a result, the detection region DR is demarcated in the optical image 40 (step ST140). The image detection region information 85 is output to the display controller 79 from the first demarcation unit 77.

As shown in FIGS. 8 and 9, in the second demarcation unit 78, the feature point extraction processing 90 and the portion-of-interest extraction processing 92 are performed on the optical image 40 to extract the portion of interest POI (here, the prominent vertebra point). Then, as shown in FIG. 10, the imaging region IR is demarcated in the optical image 40 based on the portion of interest POI by the second demarcation unit 78 (step ST150). The imaging region information 86, which is the information of the demarcated imaging region IR, is output to the display controller 79 from the second demarcation unit 78.

As shown in FIGS. 11 to 13, the optical image 40 is displayed in the display region 98 of the information display screen 95 under the control of the display controller 79. The frame 100 indicating the detection region DR and the frame 101 indicating the imaging region IR are displayed on the optical image 40 in a superimposed manner (step ST160). The operator OP adjusts the position of the electronic cassette 11 such that the imaging region IR is included within the detection region DR while confirming each of the frames 100 and 101 of the optical image 40 in the display region 98. The series of processing of steps ST120 to ST160 are repeatedly performed until the imaging instruction button 99 on the information display screen 95 is turned off by the operator OP (YES in step ST170) and an imaging stop instruction is transmitted to the camera 13 (step ST180).

After the imaging preparation work ends, the operator OP instructs the subject H to inhale and stop. Thereafter, the operator OP operates the irradiation switch 16 to instruct the radiation source 15 to start irradiation with the radiation R. As a result, the radiation R is emitted from the radiation source 15 toward the subject H.

The radiation R transmitted through the subject H reaches the electronic cassette 11. Then, the radiation R is detected as the radiation image 66 by the detection panel 35 of the electronic cassette 11. The radiation image 66 is output to the console 12 from the electronic cassette 11. Then, on the console 12, various types of image processing are performed on the radiation image 66 from the electronic cassette 11. Thereafter, the radiation image 66 is displayed in the display region 98 instead of the optical image 40.

As described above, the CPU 57 of the console 12 comprises the first acquisition unit 75, the first demarcation unit 77, the second demarcation unit 78, and the display controller 79. The first acquisition unit 75 acquires the optical image 40 in which both the electronic cassette 11 in which the detection panel 35 for detecting the radiation R is built in the portable housing 30 and the subject H facing the radiography using the electronic cassette 11 are shown, from the camera 13. The first demarcation unit 77 demarcates the detection region DR of the radiation R by the detection panel 35, the detection region DR being determined in accordance with the position of the electronic cassette 11, in the optical image 40. The second demarcation unit 78 demarcates the imaging region IR which is the region to be imaged in the radiography, the imaging region IR being determined in accordance with the position of the subject H, in the optical image 40. The display controller 79 performs control of displaying the frame 100 indicating the detection region DR and the frame 101 indicating the imaging region IR on the touch panel display 59 in a manner of being superimposed on the optical image 40.

Therefore, the operator OP can adjust the position of the electronic cassette 11 such that the imaging region IR is included in the detection region DR. Therefore, it is possible to contribute to more accurate positioning of the electronic cassette 11 with respect to the subject H. It is particularly suitable in a case in which the electronic cassette 11 is covered and hidden by the subject H and it is difficult to visually recognize the electronic cassette 11 as in the example of the chest portion decubitus front surface imaging. It is possible to reduce a concern that a situation occurs in which the imaging is performed in a state in which the detection region DR does not cover the imaging region IR. In addition, since the positioning of the electronic cassette 11 can be easily performed, a time required for the radiography can be shortened, and the stress on the subject H due to the restraint for a long time can be reduced.

The first demarcation unit 77 demarcates the detection region DR based on the detection result 46 of the radio wave receiver 36 which is the position detection sensor that detects the position of the electronic cassette 11, more specifically, the bed detection region information 47 derived from the detection result 46. Therefore, the detection region DR can be easily demarcated.

The second demarcation unit 78 extracts the portion of interest POI of the subject H included in the optical image 40, and demarcates the imaging region IR based on the portion of interest POI. Therefore, the imaging region IR can be more accurately demarcated than in a case in which the imaging region IR is directly demarcated from the optical image 40.

Modification Example

Figure 15:
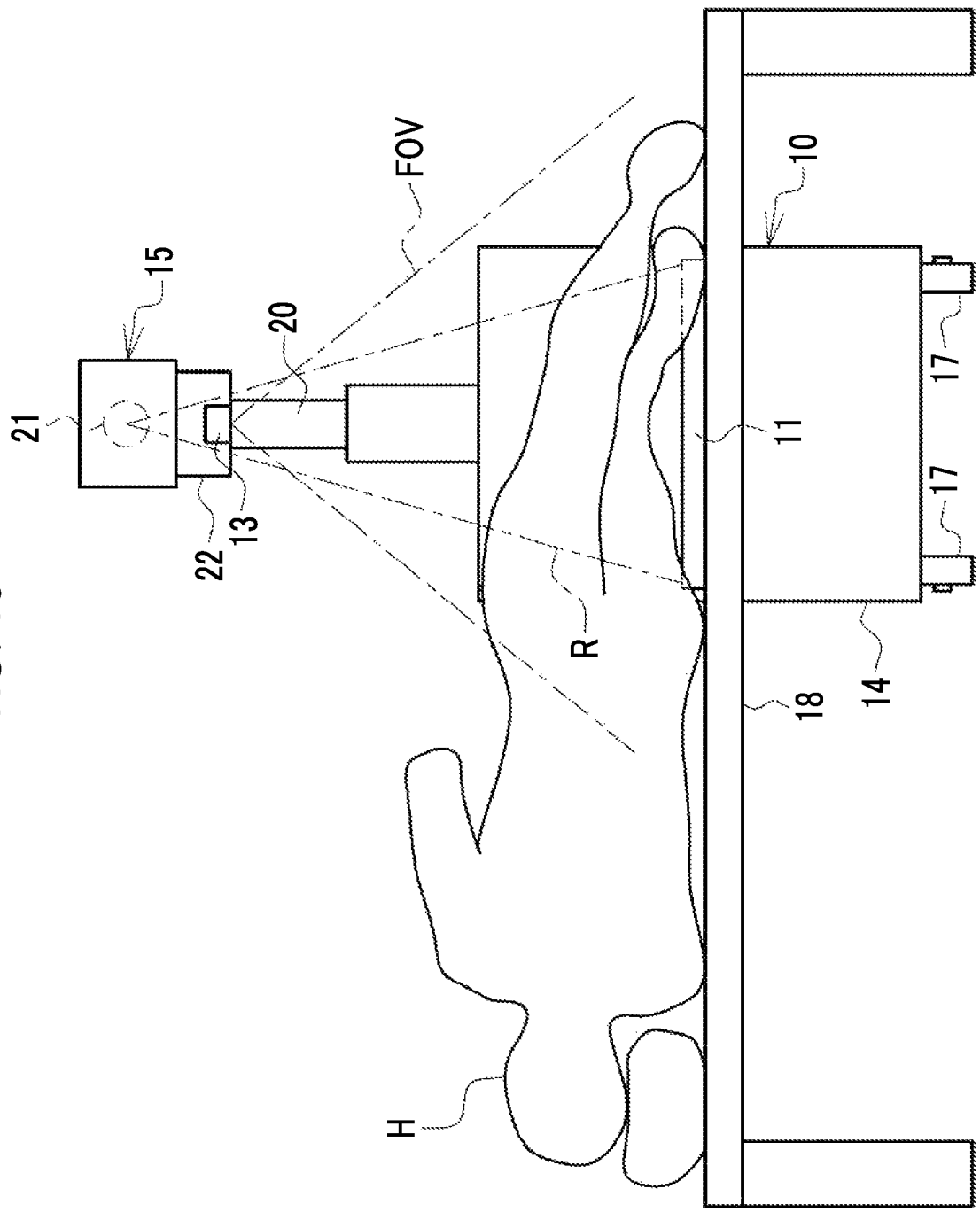
FIG. 15 is a view showing a state of knee decubitus side surface imaging.

The case of the chest portion decubitus front surface imaging has been described as an example so far, but in this modification example, a case of knee decubitus side surface imaging will be described. In this case, as shown in FIG. 15, as an example, the subject H lies down on his/her side on the bed 18 in a state in which the knee imaged by the radiography, in this case, the left knee is left down and bent. The operator OP uses an auxiliary tool, such as a cushion and/or a table, as necessary in order to maintain the posture of the subject H.

Figure 16:
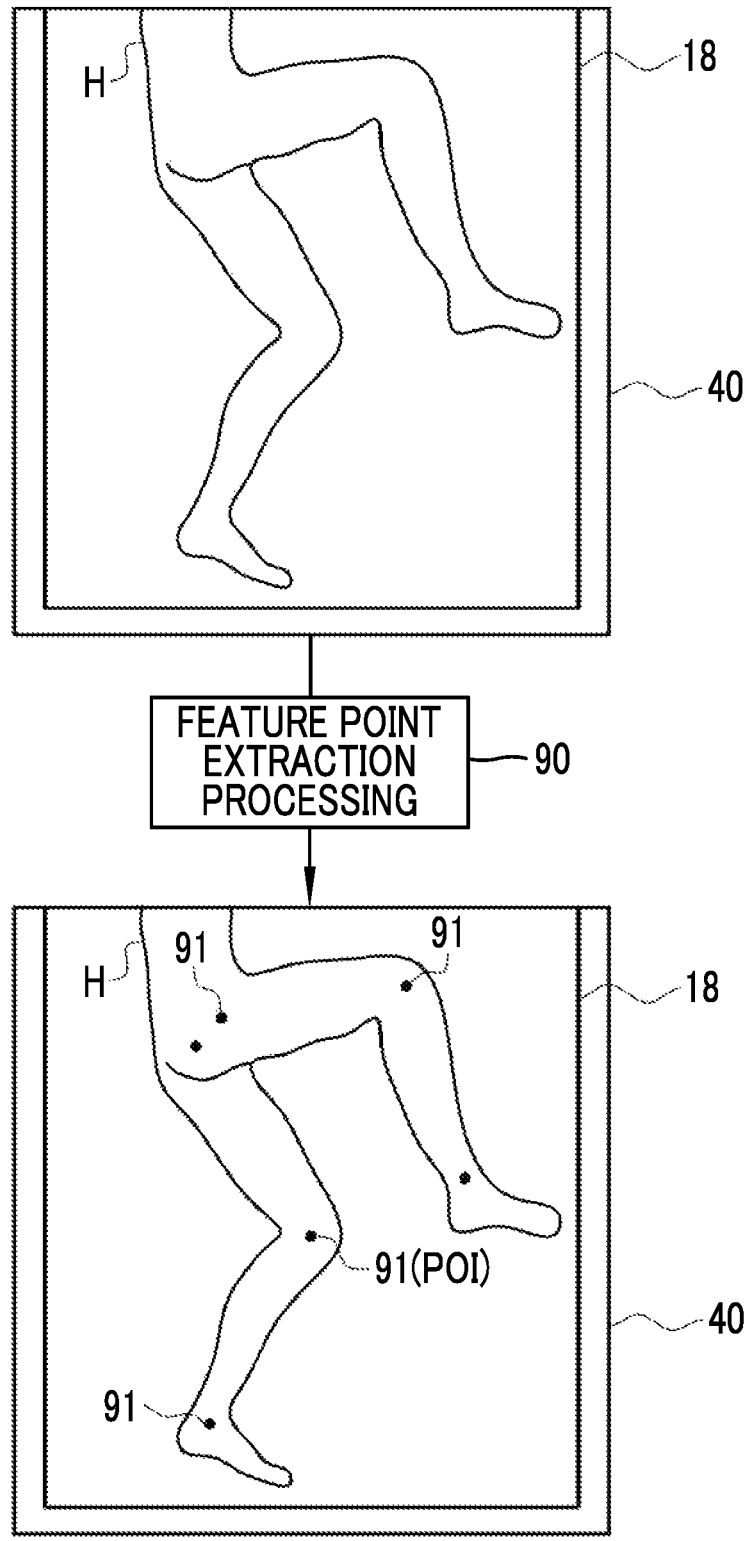
FIG. 16 is a diagram showing processing of the second demarcation unit in a case of the knee decubitus side surface imaging.

As shown in FIG. 16 as an example, in the optical image 40 in this case, about ½ of the bed 18 and from the waist of the subject H lying down on his/her side on the bed 18 to the toes of the feet, that is, a part of the upper body and the entire lower body are shown. The second demarcation unit 78 performs the feature point extraction processing 90 on the optical image 40, and extracts the right and left hip joint points, the right and left knee joint points, and the right and left ankle joint points as the feature points 91. The ankle joint point is the connection point between the shinbone and a talus. The second demarcation unit 78 extracts a left knee joint point of the feature points 91 as the portion of interest POI. Therefore, the left knee joint point is also the feature point 91 and is also an example of a "portion of interest" according to the technology of the present disclosure. In addition, the feature point extraction processing 90 is also the portion-of-interest extraction processing 92.

Figure 17:
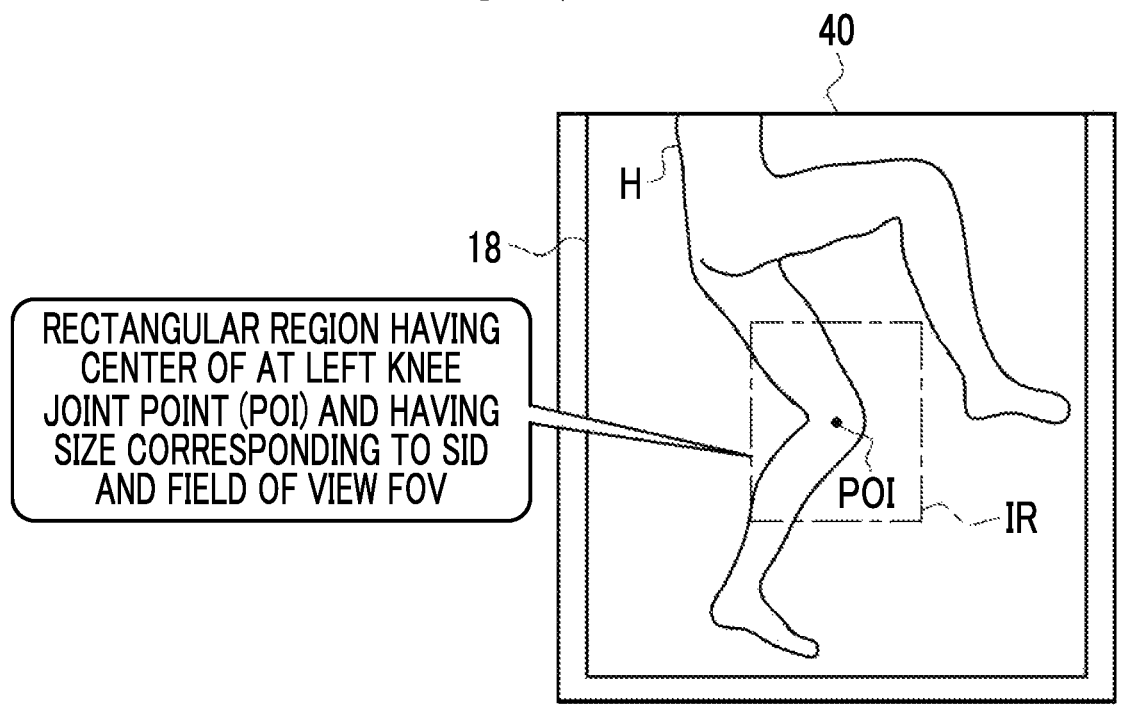
FIG. 17 is a diagram showing the processing of the second demarcation unit in a case of the knee decubitus side surface imaging.

As shown in FIG. 17 as an example, the second demarcation unit 78 demarcates a rectangular region which has a center at the left knee joint point, the rectangular region having a size corresponding to the SID and the field of view FOV of the camera 13, as the imaging region IR. Although not shown, the second demarcation unit 78 outputs the position coordinates OI_IRP1 (X, Y) to OI_IRP4 (X, Y) of the four vertexes IRP1 to IRP4 of the imaging region IR as the imaging region information 86, as display controller 79.

As described above, the imaging part is not limited to the chest portion but may be the knee. In addition to the chest portion and knee, the imaging part may be a head portion, a neck portion, an abdomen portion, a waist portion, a shoulder, an elbow, a hand, an ankle, or the like, although illustration and detailed description are omitted. Similarly, the imaging posture of the subject H does not have to be in the decubitus as shown in the example, and may be the upright or the sitting. The imaging direction is not limited to the front surface and the side surface, and may be the back surface.

Second Embodiment

Figure 18:
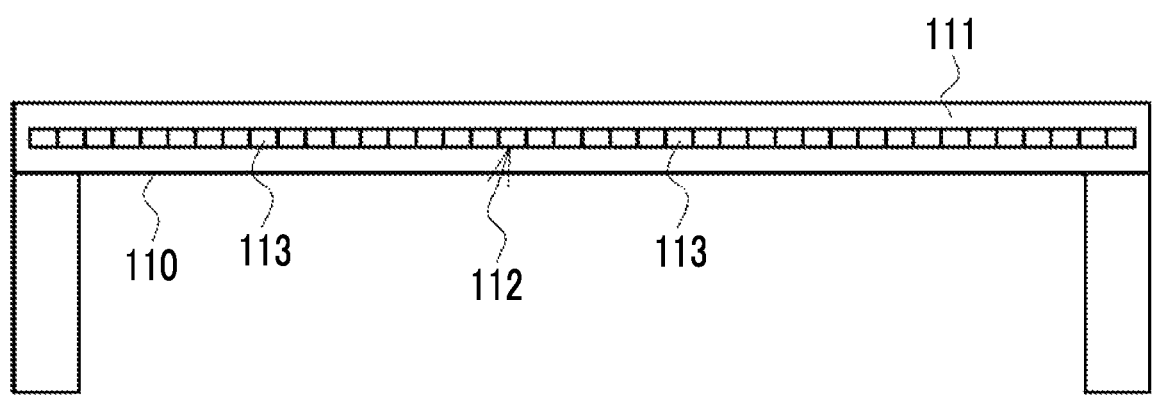
FIG. 18 is a diagram showing the bed provided with an optical display on a side portion along a long side direction.

As shown in FIG. 18 as an example, a bed 110 according to the second embodiment is provided with an optical display 112 on a side portion 111 along the long side direction thereof. The optical display 112 has a configuration in which a plurality of light sources 113 are arranged without gaps along the long side direction of the bed 18. The light source 113 is, for example, a light-emitting diode (LED).

Figure 19:
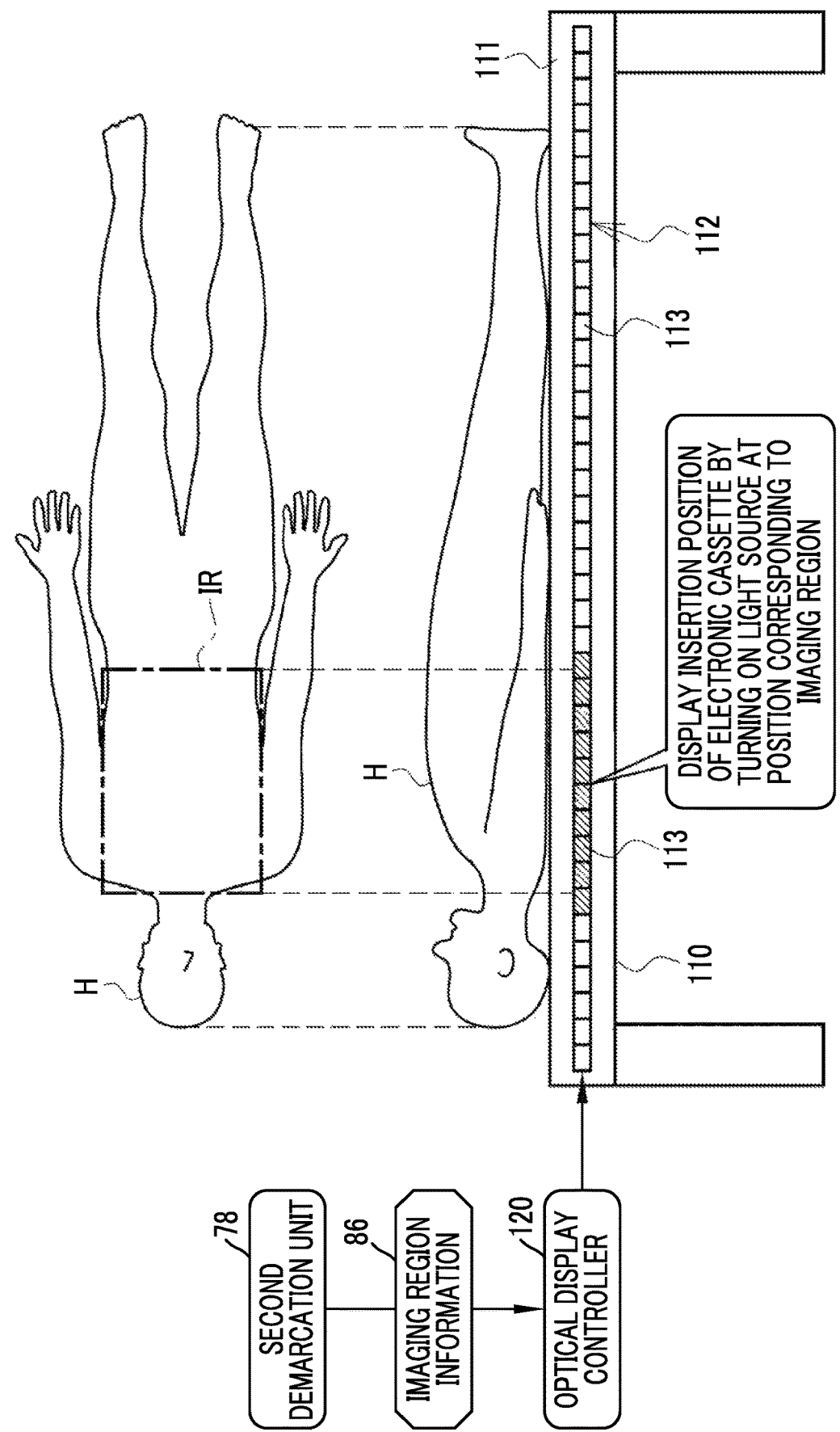
FIG. 19 is a diagram showing a state in which the optical display is operated to display an insertion position of the electronic cassette corresponding to an imaging region.

As shown in FIG. 19 as an example, the CPU 57 of the console 12 according to the second embodiment functions as an optical display controller 120, in addition to the processing units 75 to 79 according to the first embodiment (not shown except for the second demarcation unit 78). The optical display controller 120 controls an operation of the optical display 112. The imaging region information 86 is input to the optical display controller 120 from the second demarcation unit 78. The optical display controller 120 converts the position coordinates OI_IRP1 (X, Y) to OI_IRP4 (X, Y) of the vertexes IRP1 to IRP4 of the imaging region IR of the imaging region information 86 into the bed position coordinates BI_IRP1 (x, y) to BI_IRP4 (x, y) by using an inverse function $F^{-1}$ of the function F shown in FIG.

7. The optical display controller 120 operates the optical display 112 to turn on, for example, all the light sources 113 at positions including the y-coordinates of the bed position coordinates BI_IRP1 (x, y) and BI_IRP3 (x, y) to display an insertion position of the electronic cassette 11 corresponding to the imaging region IR.

As described above, in the second embodiment, in a state in which the subject H lies down on the bed 18, in a case in which the electronic cassette 11 is inserted between the subject H and the bed 18 and the radiography is performed, the optical display controller 120 operates the optical display 112 that displays light for the position adjustment of the electronic cassette 11 on the side portion 111 along the long side direction of the bed 18 to display the insertion position of the electronic cassette 11 corresponding to the imaging region IR. Therefore, the operator OP can grasp at a glance from where the electronic cassette 11 should be inserted, and the position adjustment of the electronic cassette 11 is further improved.

The optical display is not limited to the optical display 112 in which the plurality of light sources 113 described as an example are connected. A projector that projects light for position adjustment of the electronic cassette 11 onto the side portion 111 may be used.

In a case in which the radiography is to be performed in a state in which the imaging region IR is not included in the detection region DR, a message indicating a state in which the imaging region IR is not included in the detection region DR is displayed on the information display screen 95 and the notification may be performed with respect to the operator OP. The operator OP may be notified by voice of a state in which the imaging region IR is not included in the detection region DR. In addition, an indicator, such as a warning lamp, may be used for the notification. Alternatively, in a case in which radiography is to be performed in a state in which the imaging region IR is not included in the detection region DR, the irradiation with the radiation R by the radiation source 15 may be prohibited.

The indicator indicating the detection region DR is not limited to the frame 100 described as an example. An L-shaped line representing the four vertexes DRP1 to DRP4 of the detection region DR may be used. Also, the indicator indicating the imaging region IR is not limited to the frame 101 described as an example, and an L-shaped line representing the four vertexes IRP1 to IRP4 of the imaging region IR may be used.

The position detection sensor is not limited to the radio wave receiver 36 described as an example. The position of the electronic cassette 11 may be detected by pressure-sensitive sensors arranged in a two-dimensional matrix on the surface of the top plate of the bed 18. In addition, a marker may be attached to the surface of the electronic cassette 11 and the image recognition may be performed on the marker shown in the optical image 40 to detect the position of the electronic cassette 11. In this case, the camera 13 serves as the position detection sensor.

The light sources may be arranged in a row along the side portion of the bed 18, a light receiving sensor may be provided on the side portion opposite to the light source, and the position of the electronic cassette 11 may be detected by a light shielding state of the electronic cassette 11. In addition, the position of the electronic cassette 11 may be detected by an ultrasound sensor. In short, the position detection sensor may be any device as long as the position of the electronic cassette 11 can be detected.

Examples of the portion of interest POI include the following in addition to the prominent vertebra point and the like described as an example. That is, examples thereof include laryngeal prominence (thyroid cartilage) in a case in which the imaging part is the head portion, suprasternal space, shoulder blade lower end, xiphoid process, and rib lower edge in which the imaging part is the chest portion, iliac crest upper edge (line connecting right and left iliac crests (Jacoby's line)), anterior superior iliac spine, pubic symphysis/greater trochanter, and coccyx in a case in which the imaging part is the waist portion. These examples are so-called body surface indicators.

An installation position of the camera 13 is not limited to the radiation source 15. A ceiling, a wall, or the like of the hospital room may be used. In addition, although the mobile radiation generation device 10 has been described as an example, the present disclosure is not limited to this. A radiation generation device installed in the radiography room may be used.

The console 12 may be built in the mobile radiation generation device 10. In this case, various screens, such as the information display screen 95, may be transmitted to a portable terminal, such as a tablet terminal owned by the operator, from the console 12, for example, in a form of screen data for web distribution created by markup language, such as extensible markup language (XML). In this case, the portable terminal reproduces various screens to be displayed on the web browser based on the screen data and displays the screens on the display. It should be noted that, instead of the XML, another data description language, such as Javascript (registered trademark) object notation (JSON), may be used.

It is possible to make various modifications with respect to the hardware configuration of the computer constituting the imaging support apparatus according to the technology of the present disclosure. For example, the imaging support apparatus can be composed of a plurality of computers separated as hardware in order to improve the processing capacity and the reliability. For example, the functions of the first acquisition unit 75 and the second demarcation unit 78 and the functions of the second acquisition unit 76, the first demarcation unit 77, and the display controller 79 are distributed to two computers and carried out. In this case, the two computers constitute the imaging support apparatus.

As described above, the hardware configuration of the computer of the imaging support apparatus can be appropriately changed in accordance with required performance, such as processing capacity, safety, and reliability. Further, it is needless to say that, in addition to the hardware, an application program, such as the operation program 70, can be duplicated or distributed and stored in a plurality of storages for the purpose of securing the safety and the reliability.

In each of the embodiments described above, as the hardware structure of the processing units that execute various processing, such as the first acquisition unit 75, the second acquisition unit 76, the first demarcation unit 77, the second demarcation unit 78, the display controller 79, and the optical display controller 120, the following various processors can be used. As described above, the various processors include, in addition to the CPU 57, which is a general-purpose processor that executes software (operation program 70) to function as the various processing units, a programmable logic device (PLD), which is a processor of which a circuit configuration can be changed after the manufacturing, such as a field programmable gate array (FPGA), a dedicated electric circuit, which is a processor having a circuit configuration designed exclusively for executing specific processing, such as an application specific integrated circuit (ASIC), and the like.

One processing unit may be composed of one of various processors described above or may be composed of a combination of two or more processors (for example, a combination of a plurality of ASICs and/or a combination of an ASIC and a FPGA) of the same type or different types. In addition, a plurality of the processing units may be composed of one processor.

As an example in which the plurality of processing units are composed of one processor, firstly, as represented by a computer, such as a client and a server, there is a form in which one processor is composed of a combination of one or more CPUs and software, and the processor functions as the plurality of processing units. Second, as represented by a system on chip (SoC) or the like, there is a form in which a processor, which realizes the functions of the entire system including the plurality of processing units with a single integrated circuit (IC) chip, is used. As described above, various processing units are composed of one or more of the various processors as the hardware structure.

Further, as the hardware structure of these various processors, more specifically, it is possible to use an electric circuit (circuitry) in which circuit elements, such as semiconductor elements, are combined.

The technology of the present disclosure can also be appropriately combined with various embodiments and/or various modification examples described above. In addition, it is needless to say that the present disclosure is not limited to each of the embodiments described above, various configurations can be adopted as long as the configuration does not deviate from the gist. Further, the technology of the present disclosure includes, in addition to the program, a storage medium that stores the program in a non-transitory manner.

The described contents and shown contents above are the detailed description of the parts according to the technology of the present disclosure, and are merely an example of the technology of the present disclosure. For example, the above description of the configuration, the function, the action, and the effect are the description of examples of the configuration, the function, the action, and the effect of the parts according to the technology of the present disclosure. Accordingly, it is needless to say that unnecessary parts may be deleted, new elements may be added, or replacements may be made with respect to the described contents and shown contents above within a range that does not deviate from the gist of the technology of the present disclosure. In addition, in order to avoid complications and facilitate grasping the parts according to the technology of the present disclosure, in the described contents and shown contents above, the description of technical general knowledge and the like that do not particularly require description for enabling the implementation of the technology of the present disclosure are omitted.

In the present specification, "A and/or B" is synonymous with "at least one of A or B". That is, "A and/or B" means that it may be only A, only B, or a combination of A and B. In addition, in the present specification, also in a case in which three or more matters are associated and expressed by "and/or", the same concept as "A and/or B" is applied.

All documents, patent applications, and technical standards described in the present specification are incorporated herein by reference to the same extent as in a case in which each document, each patent application, and each technical standard are specifically and individually described by being incorporated by reference.

What is claimed is:

1. An imaging support apparatus comprising:
a processor,
wherein the processor
acquires an optical image in which both an electronic cassette in which a detection panel for detecting radiation is built in a portable housing and a subject facing radiography using the electronic cassette are shown, from a camera,
demarcates a detection region of the radiation by the detection panel, the detection region being determined in accordance with a position of the electronic cassette, in the optical image,
demarcates an imaging region which is a region to be imaged in the radiography, the imaging region being determined in accordance with a position of the subject, in the optical image, and
performs control of displaying an indicator indicating the detection region and an indicator indicating the imaging region on a display in a manner of being superimposed on the optical image.

2. The imaging support apparatus according to claim 1, wherein the processor demarcates the detection region based on a detection result of a position detection sensor that detects the position of the electronic cassette.

3. The imaging support apparatus according to claim 1, wherein the processor
extracts a portion of interest of the subject included in the optical image, and
demarcates the imaging region based on the portion of interest.

4. The imaging support apparatus according to claim 1, wherein, in a state in which the subject lies down on a bed, in a case in which the electronic cassette is inserted between the subject and the bed and the radiography is performed, the processor operates an optical display that displays light for position adjustment of the electronic cassette on a side portion along a long side direction of the bed to display an insertion position of the electronic cassette corresponding to the imaging region.

5. An operation method of an imaging support apparatus, the method comprising:
acquiring an optical image in which both an electronic cassette in which a detection panel for detecting radiation is built in a portable housing and a subject facing radiography using the electronic cassette are shown, from a camera;
demarcating a detection region of the radiation by the detection panel, the detection region being determined in accordance with a position of the electronic cassette, in the optical image;
demarcating an imaging region which is a region to be imaged in the radiography, the imaging region being determined in accordance with a position of the subject, in the optical image; and
performing control of displaying an indicator indicating the detection region and an indicator indicating the imaging region on a display in a manner of being superimposed on the optical image.

6. A non-transitory computer-readable storage medium storing an operation program of an imaging support apparatus, the program causing a computer to execute a process comprising:
acquiring an optical image in which both an electronic cassette in which a detection panel for detecting radiation is built in a portable housing and a subject facing radiography using the electronic cassette are shown, from a camera;

demarcating a detection region of the radiation by the detection panel, the detection region being determined in accordance with a position of the electronic cassette, in the optical image;

demarcating an imaging region which is a region to be imaged in the radiography, the imaging region being determined in accordance with a position of the subject, in the optical image; and performing control of displaying an indicator indicating the detection region and an indicator indicating the imaging region on a display in a manner of being superimposed on the optical image.

* * * * *